US010052347B2

(12) United States Patent
Mogielnicki et al.

(10) Patent No.: US 10,052,347 B2
(45) Date of Patent: Aug. 21, 2018

(54) USE OF A BLOCK POLYMER COMPRISING A BLOCK OF POLY(3-(METHACRYLOYLAMINO) PROPYLTRIMETHYLAMMONIUM CHLORIDE) (PMAPTAC) FOR THE NEUTRALIZATION OF HEPARIN

(71) Applicants: UNIWERSYTET JAGIELLONSKI, Cracow (PL); UNIWERSYTET MEDYCZNY W BIALYMSTOKU, Bialystok (PL)

(72) Inventors: Andrzej Mogielnicki, Bialystok (PL); Bartlomiej Kalaska, Garwolin (PL); Dariusz Pawlak, Bialystok (PL); Emilia Sokolowska, Bialystok (PL); Maria Nowakowska, Cracow (PL); Krzysztof Szczubialka, Krzywaczka (PL); Kamil Kaminski, Makow Podhalanski (PL)

(73) Assignees: UNIWERSYTET JAGIELLONSKI, Cracow (PL); UNIWERSYTET MEDYCZNY W BIALYMSTOKU, Bialystok (PL)

( * ) Notice: Subject to any disclaimer, the term of this patent is extended or adjusted under 35 U.S.C. 154(b) by 0 days.

(21) Appl. No.: 15/579,277

(22) PCT Filed: Jun. 9, 2016

(86) PCT No.: PCT/PL2016/050028
§ 371 (c)(1),
(2) Date: Dec. 4, 2017

(87) PCT Pub. No.: WO2016/200284
PCT Pub. Date: Dec. 15, 2016

(65) Prior Publication Data
US 2018/0161361 A1   Jun. 14, 2018

(30) Foreign Application Priority Data
Jun. 10, 2015   (PL) ..................................... P.412654

(51) Int. Cl.
*A61K 31/785* (2006.01)
*C08L 33/24* (2006.01)
*A61P 11/00* (2006.01)
*C07H 5/06* (2006.01)

(52) U.S. Cl.
CPC ............ *A61K 31/785* (2013.01); *C08L 33/24* (2013.01); *A61P 11/00* (2018.01); *C07H 5/06* (2013.01); *C08F 2438/02* (2013.01); *C08F 2438/03* (2013.01)

(58) Field of Classification Search
CPC .... H05B 6/6482; A01N 37/12; A61K 31/785; C08L 33/24
See application file for complete search history.

(56) References Cited

U.S. PATENT DOCUMENTS

2010/0155323 A1   6/2010   Weiss et al. ............... 210/321.6

FOREIGN PATENT DOCUMENTS

| EP | 2 842 548 A1 | 3/2015 | ............... A61K 9/19 |
| PL | P.387249 A | 8/2010 | |
| PL | P.391043 A | 10/2011 | |
| WO | WO 95/34588 | 12/1995 | ............ C08F 220/34 |
| WO | WO 2010/074702 A1 | 7/2010 | ............... C07K 1/32 |

OTHER PUBLICATIONS

Banerjee et al.; *Synthesis of PEG containing cationic block copolymers and their interaction with human serum albumin*, Reactive & Functional Polymers 74; Jan. 2014; pp. 81-89.
Banerjee et al.; *Water-soluble nanoparticles from poly(ethylene glycol)-based cationic random copolymers and double-tail surfactant*; Colloids and Surfaces A: Physiochem. Eng. Aspects 395; 2012; pp. 255-261.
Fischer; *A Biochem Zeit*; 278; 133; 1935.
Hirota et al.; *MPC-Polymer Reduces Adherence and Biofilm Formation by Oral Bacteria*; J Dent Res.; 2011; 90(7); pp. 900-905.
Hou et al.; *A Method for Extracorporeal Heparin Removal from Blood by Affinity Chromatography*; Artificial Organs; 1990; 14(6); pp. 436-442.
Ishihara et al.; *Preparation of Phospholipid Polymers and Their Properties as Polymer Hydrogel Membranes*; Polymer Journal; vol. 22, No. 5; 1990; pp. 355-360.
Iwasaki et al.; *Cell membrane-inspired phospholipid polymers for developing medical devices with excellent biointerfaces*; Science and Technology of Advanced Materials 13; 2012; 13(6); 064101.
Kaminski et al.; *Cationic Derivatives of Dextran and Hydroxypropylcellulose as Novel Potential Heparin Antagonists*; Journal of Medicinal Chemistry; 2011; 54; Aug. 2011; pp. 6586-6596.
Katakura et al.; *Evaluation of 2-methacryloyloxyethyl phosphorylcholine (MPC) polymer coated dressing on surgical wounds*; J Med Dent Sci 2005; 52; pp. 115-121.
Kolde et al.; *Ein einfaches und spezifisches Verfahren zur Entfernung von Heparin aus Zitratplasma*; (Translated: A simple and specific method for removing heparin from citrated plasma) Hamostaseologie 1994; 14(10); pp. 37-43.
Kreppel et al.; *Modification of Adenovirus Gene Transfer Vectors With Synthetic Polymers: A Scientific Review and Technical Guide*; Molecular Therapy; Vo. 16, No. 1; Jan. 2008; pp. 16-29.
Ma et al.; *Heparin Removal from Blood Using Poly($_L$-lysine) Immobilized Hollow Fiber*; Biotechnology and Bioengineering; vol. 40; Mar. 1992; pp. 530-536.

(Continued)

*Primary Examiner* — Alma Pipic
(74) *Attorney, Agent, or Firm* — Renner, Kenner, Greive, Bobak, Taylor & Weber

(57) ABSTRACT

The subject of the invention is use of block polymers with a block of poly(3-methacryloylpropyltrimethylammonium chloride) to direct neutralization of heparin, especially unfractionated heparin and low molecular weight heparins in the blood and other body fluids.

12 Claims, 32 Drawing Sheets

(56) References Cited

OTHER PUBLICATIONS

Varghese et al.; *Efficiency of Polymer Beads in the Removal of Heparin: Toward the Development of a Novel Reactor*; Artificial Cells, Blood Substitutes, and Biotechnology; 24; 2006; pp. 419-432.
Wang et al.; *A protamaine bio-reactor for extracorporeal heparin removal: In vitro modeling, function assessment, and future direction*; International Journal of Bio-Chromatography; Jan. 2001; 6(2); pp. 133-149.
Zwischenberger et al.; *Application of a Heparin Removal Device in Patients With Known Protamine Hypersensitivity*; Journal of Thoracic and Cardiovascular Surgery; vol. 115, No. 3; 1998; pp. 729-731.
Zwischenberger et al.; *Safety and efficacy of a heparin removal device: a prospective randomized preclinical outcomes study*; The Annals of Thoracic Surgery; 2001; vol. 71, Issue 1; pp. 270-277.
International Search Report dated Oct. 10, 2016 in related application No. PCT/PL2016/050028.
Written Opinion dated Oct. 10, 2016 in related application No. PCT/PL2016/050028.
Search Report dated Jul. 20, 2015 in related application No. P.412654.

Fig.1 Free (uncomplexed) UFH concentration changes according to mass ratio of polymer/UFH.
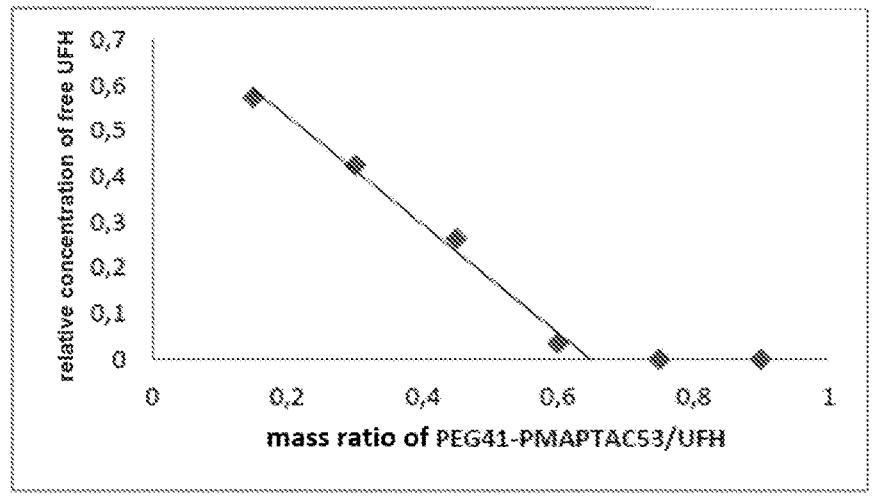
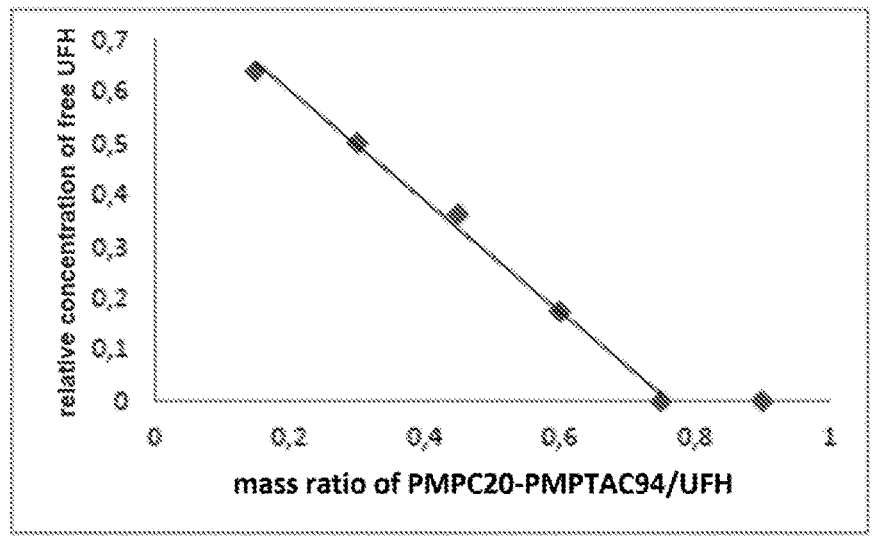

Fig. 1 Continued
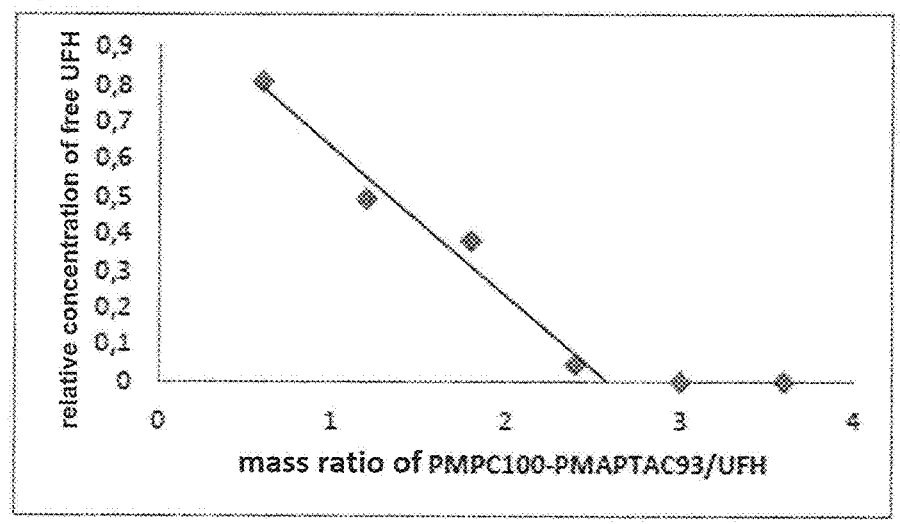
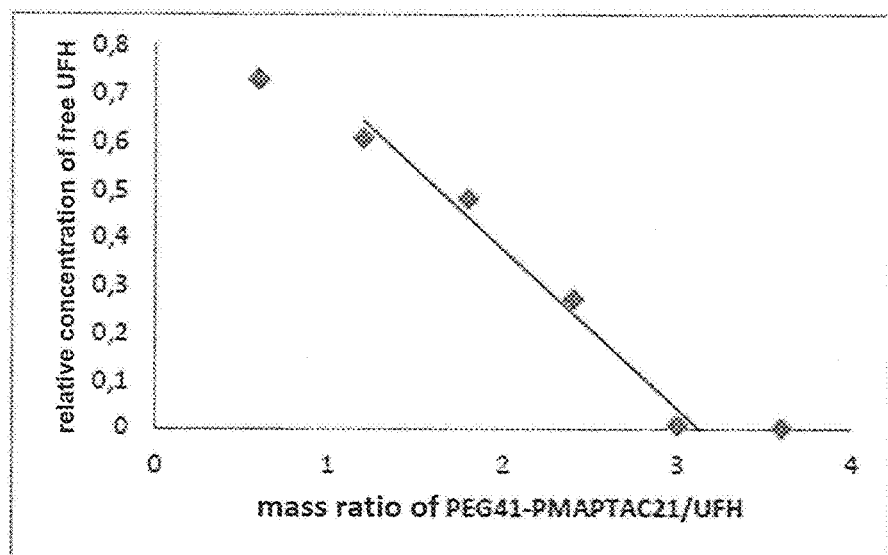

Fig.2 The size of polymers and UFH complexes measured by DLS technique.
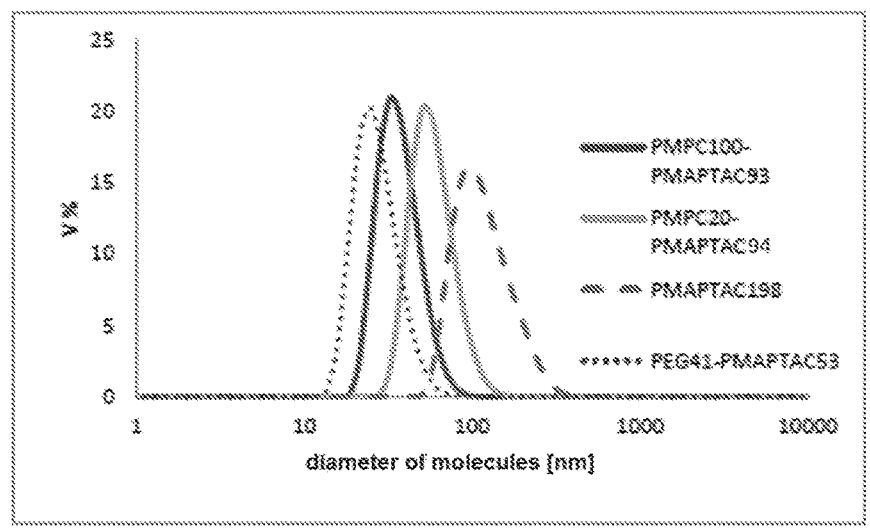
Fig.3 The size of polymer and protamine complexes with bovine serum albumin measured by DLS technique.
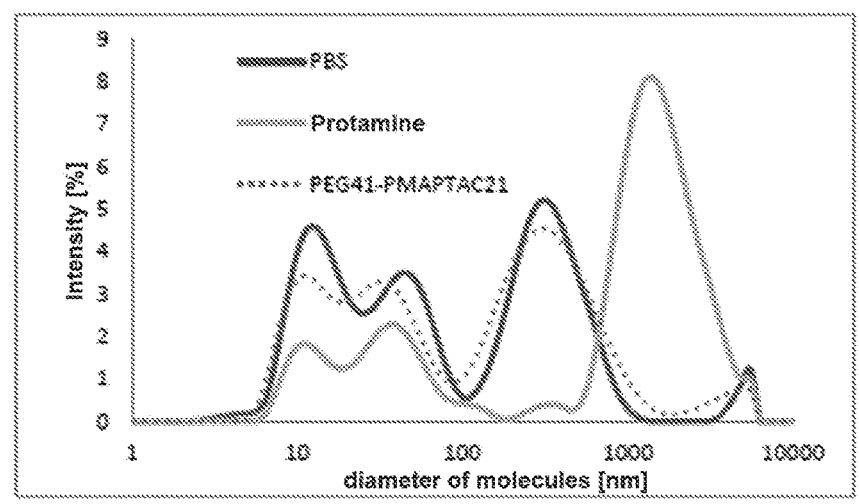

Fig. 3 Continued
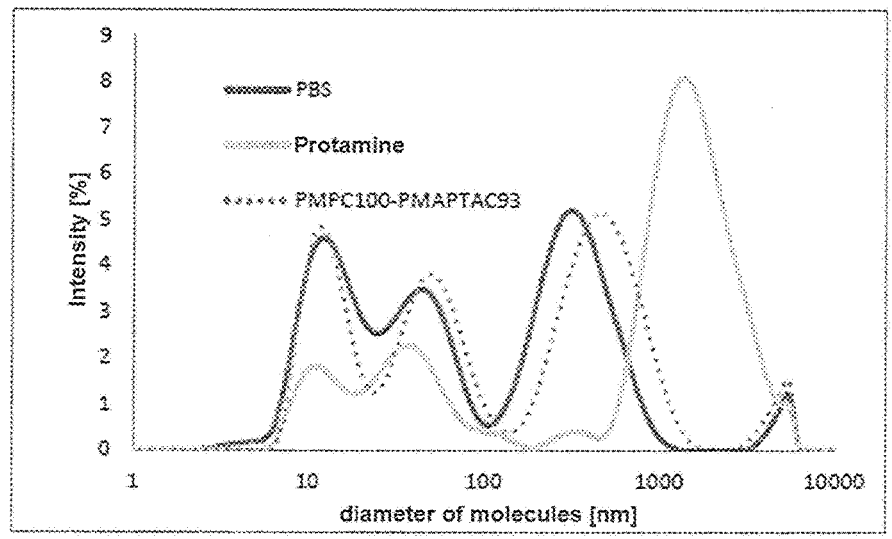
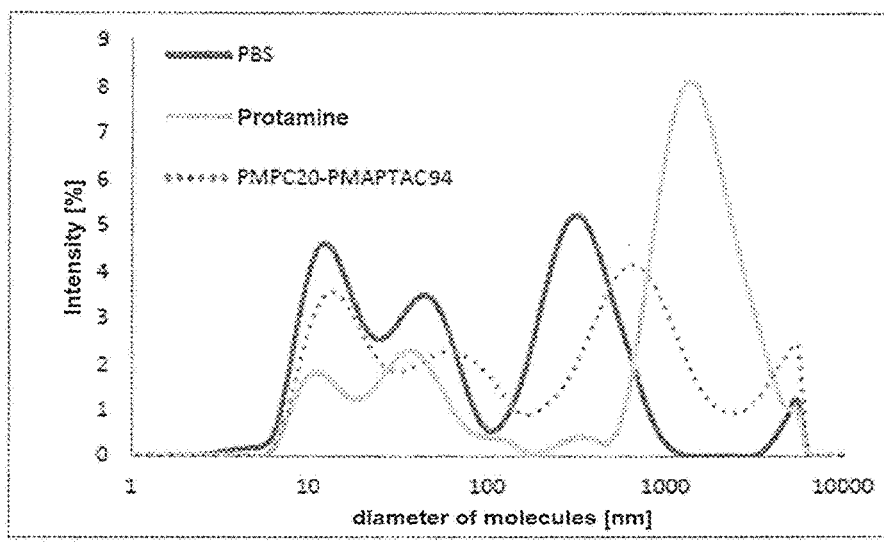

Fig.4

Thrombus weight collected from carotid artery of Wistar rat developing experimentally induced thrombosis after administration of PBS solution (vehicle), 300 U/kg unfractionated heparin (UFH), 300 U/kg UFH + 1.95 mg/kg PEG41-PMAPTAC53, 300 U/kg UFH + 9.36 mg/kg PEG41-PMAPTAC21, 300 U/kg UFH + 7.74 mg/kg PMPC100-PMAPTAC93, 300 U/kg UFH + 2.25 mg/kg PMPC20-block-PMAPTAC94, 300 U/kg UFH + 1.8 mg/kg PMAPTAC198, 300 U/kg + 7.5 mg/kg Dex40-GTMAC3 and 300 U/kg UFH + 3 mg/kg protamine; ***P<0.001 vs. vehicle; ^P<0.05, ^^P<0.01, ^^^P<0.001 vs. UFH. Data are expressed as mean ±S.E.M.

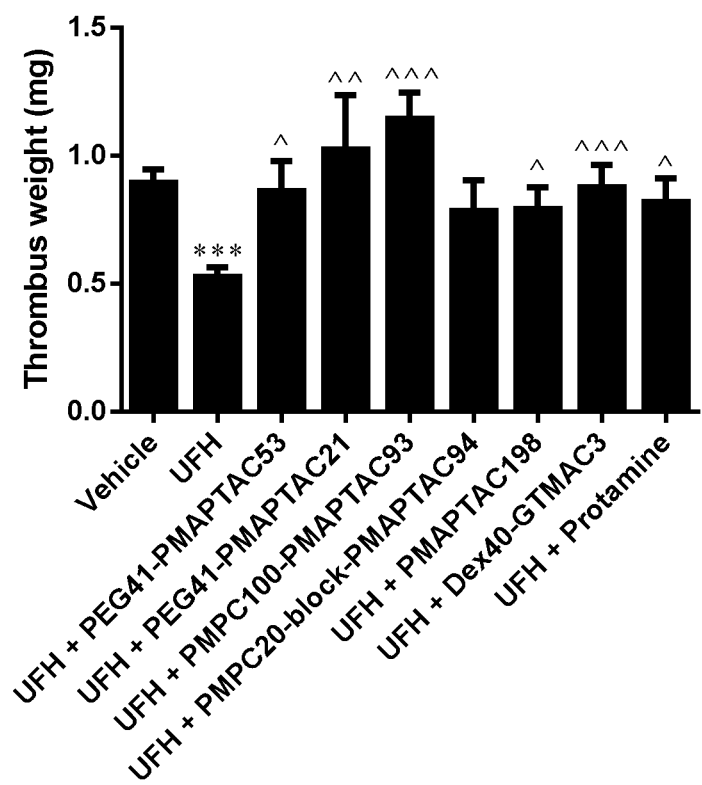

Fig.5 Bleeding time measured in tail of Wistar rats developing experimentally induced thrombosis after administration of PBS solution (vehicle), 300 U/kg unfractionated heparin (UFH), 300 U/kg UFH + 1.95 mg/kg PEG41-PMAPTAC53, 300 U/kg UFH + 9.36 mg/kg PEG41-PMAPTAC21, 300 U/kg UFH + 7.74 mg/kg PMPC100-PMAPTAC93, 300 U/kg UFH + 2.25 mg/kg PMPC20-block-PMAPTAC94, 300 U/kg UFH + 1.8 mg/kg PMAPTAC198, 300 U/kg + 7.5 mg/kg Dex40-GTMAC3 and 300 U/kg UFH + 3 mg/kg protamine; ***P<0.001 vs. vehicle; ^^P<0.01, ^^^P<0.001 vs. UFH. Data are expressed as mean ±S.E.M.

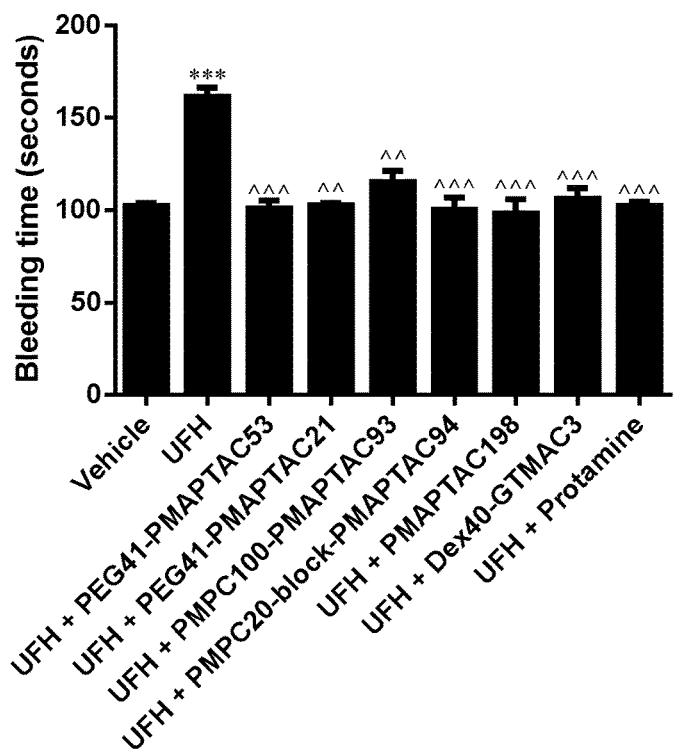

Fig. 6 Activated partial thromboplastin time (aPTT) measured in plasma collected from Wistar rats developing experimentally induced thrombosis after administration of PBS solution (vehicle), 300 U/kg unfractionated heparin (UFH), 300 U/kg UFH + 1.95 mg/kg PEG41-PMAPTAC53, 300 U/kg UFH + 9.36 mg/kg PEG41-PMAPTAC21, 300 U/kg UFH + 7.74 mg/kg PMPC100-PMAPTAC93, 300 U/kg UFH + 2.25 mg/kg PMPC20-block-PMAPTAC94, 300 U/kg UFH + 1.8 mg/kg PMAPTAC198, 300 U/kg + 7.5 mg/kg Dex40-GTMAC3 and 300 U/kg UFH + 3 mg/kg protamine; ***$P<0.001$ vs. vehicle; ^^$P<0.01$, ^^^$P<0.001$ vs. UFH. Data are expressed as mean ±S.E.M.

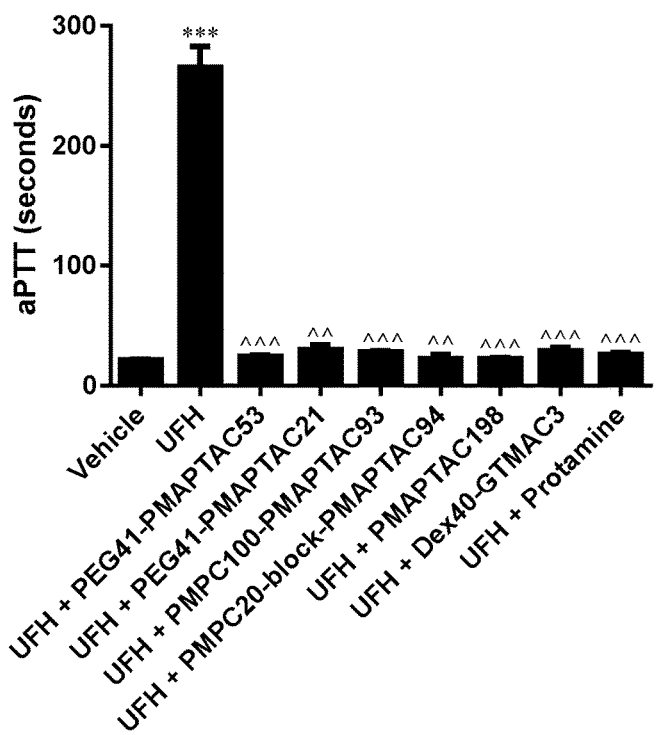

Fig.7 Anti-fXa activity in plasma collected from Wistar rats developing experimentally induced thrombosis after administration of PBS solution (vehicle), 300 U/kg unfractionated heparin (UFH), 300 U/kg UFH + 1.95 mg/kg PEG41-PMAPTAC53, 300 U/kg UFH + 9.36 mg/kg PEG41-PMAPTAC21, 300 U/kg UFH + 7.74 mg/kg PMPC100-PMAPTAC93, 300 U/kg UFH + 2.25 mg/kg PMPC20-block-PMAPTAC94, 300 U/kg UFH + 1.8 mg/kg PMAPTAC198, 300 U/kg + 7.5 mg/kg Dex40-GTMAC3 and 300 U/kg UFH + 3 mg/kg protamine; ***$P<0.001$ vs. vehicle; ^^$P<0.01$, ^^^$P<0.001$ vs. UFH. Data are expressed as mean ±S.E.M.

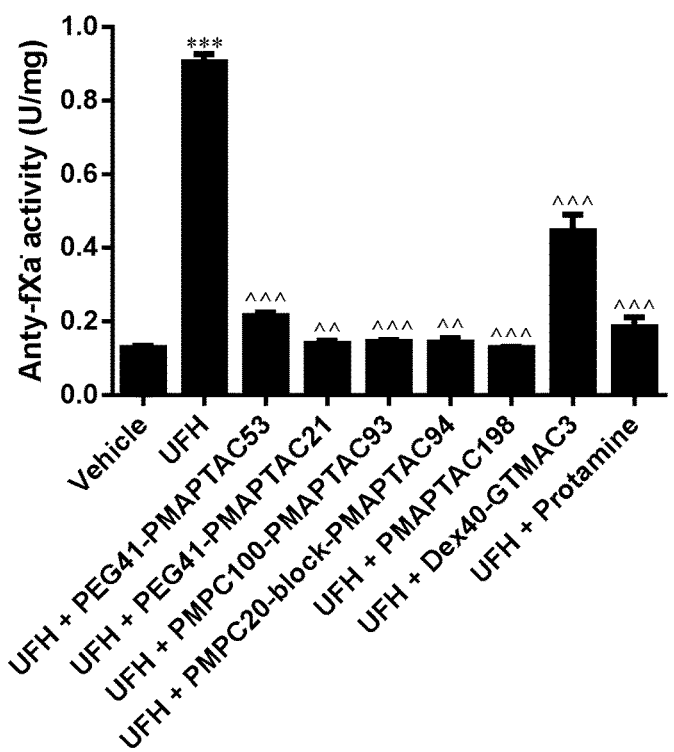

Fig. 8 Hematologic parameters: WBC (A), RBC (B), HGB (C), HCT (D), MCV (E), MCH (F), MCHC (G), PLT (H) measured after 1 hour from treatment with PBS – control group, unfractionated heparin (UFH) in a dose of 300U/kg, or 300 U/kg UFH + 1.95 mg/kg PEG41-PMAPTAC53, 300 U/kg UFH + 9.36 mg/kg PEG41-PMAPTAC21, 300 U/kg UFH + 7.74 mg/kg PMPC100-PMAPTAC93, 300 U/kg UFH + 2.25 mg/kg PMPC20-PMAPTAC94, 300 U/kg UFH + 1.8 mg/kg PMAPTAC198 or 300 U/kg + 3 mg protamine. The results are presented as mean ± SD; n=3-7.

WBC, white blood cells; RBC, red blood cells; HGB, hemoglobin; HCT, hematocrit; MCV, mean corpuscular volume; MCH, mean corpuscular hemoglobin; MCHC, mean corpuscular hemoglobin concentration; PLT, blood platelets.

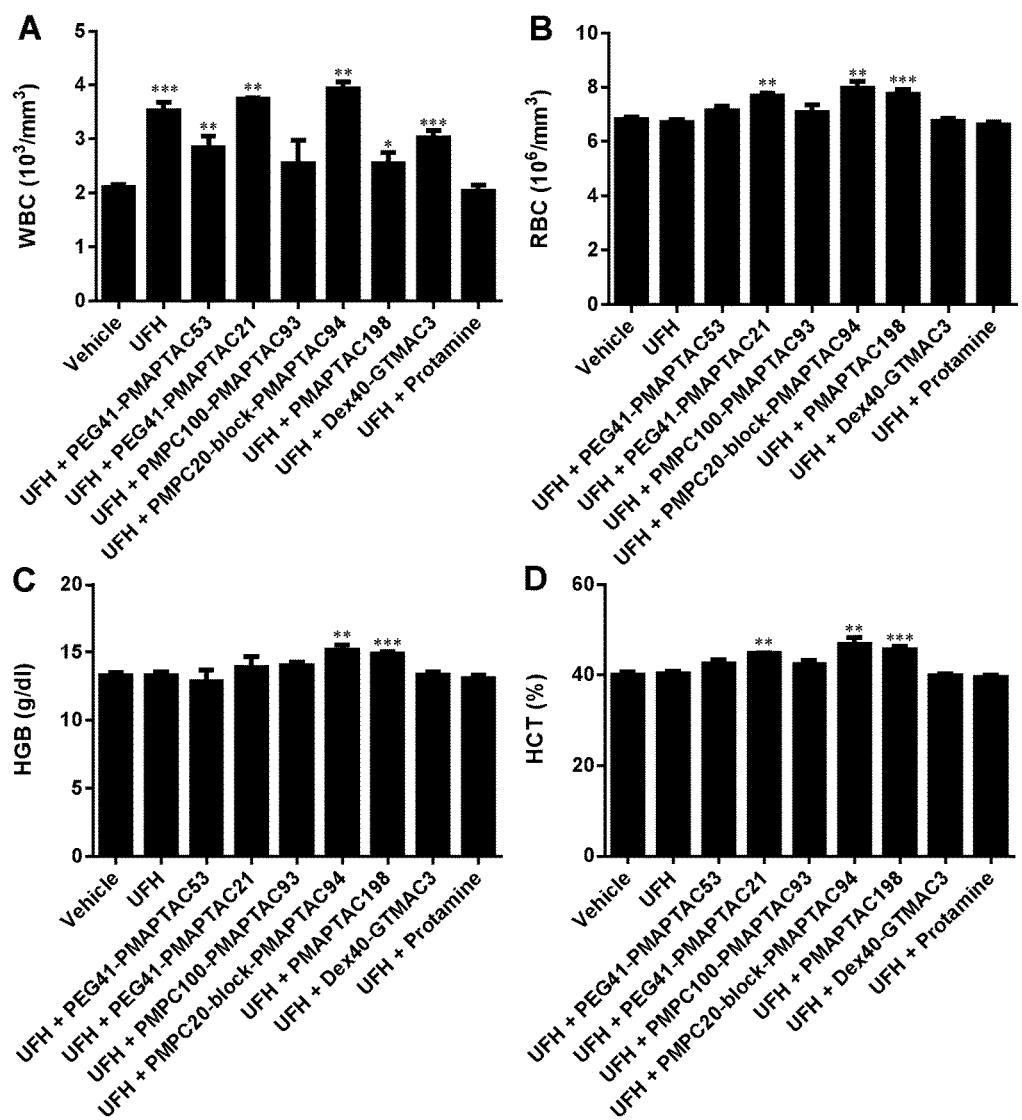

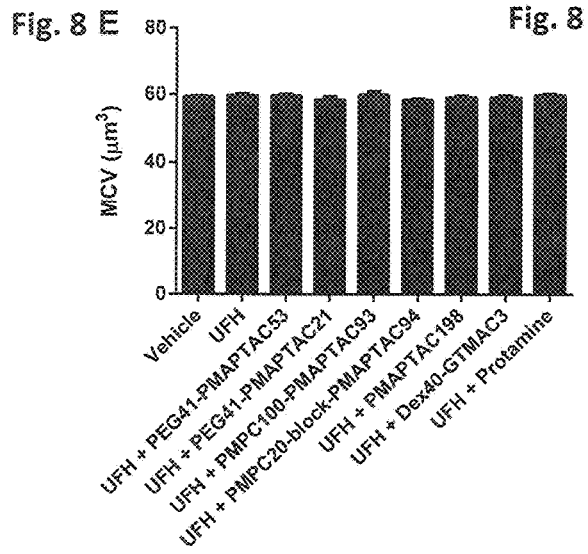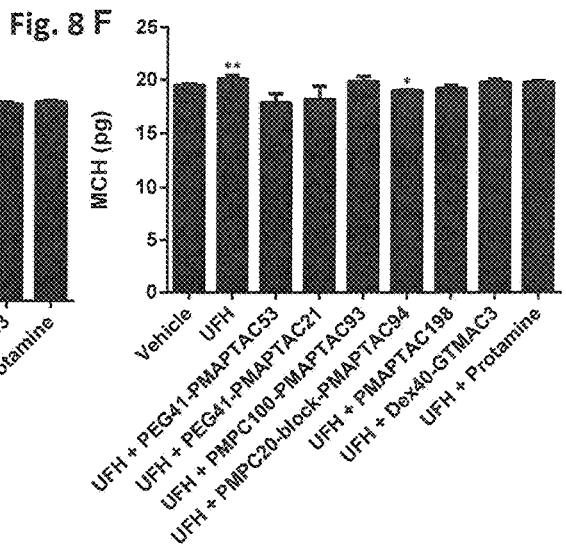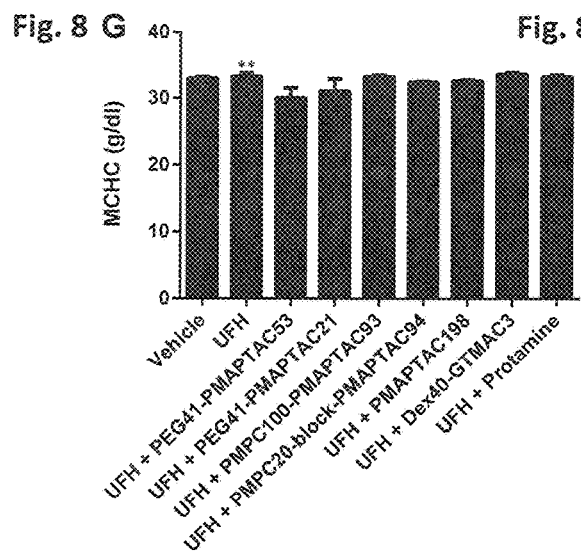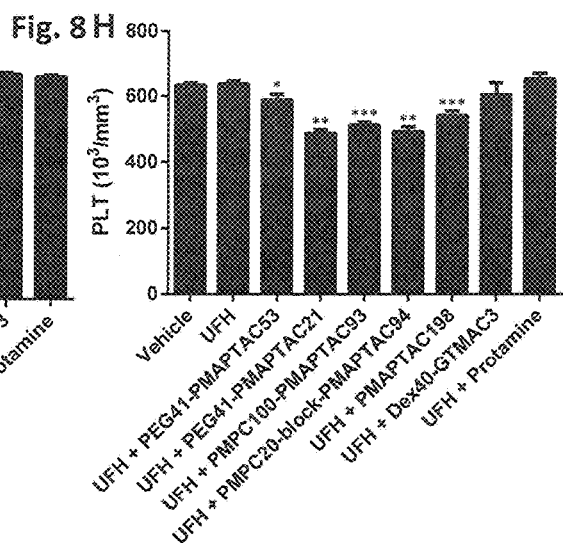

Fig.9 Effect of polymers on mean arterial blood pressure (MBP) 1 hour after administration of PBS solution (vehicle), 300 U/kg unfractionated heparin (UFH), 300 U/kg UFH + 1.95 mg/kg PEG41-PMAPTAC53, 300 U/kg UFH + 9.36 mg/kg PEG41-PMAPTAC21, 300 U/kg UFH + 7.74 mg/kg PMPC100-PMAPTAC93, 300 U/kg UFH + 2.25 mg/kg PMPC20-block-PMAPTAC94, 300 U/kg UFH + 1.8 mg/kg PMAPTAC198, 300 U/kg + 7.5 mg/kg Dex40-GTMAC3 and 300 U/kg UFH + 3 mg/kg protamine. Data are expressed as mean ±S.E.M.

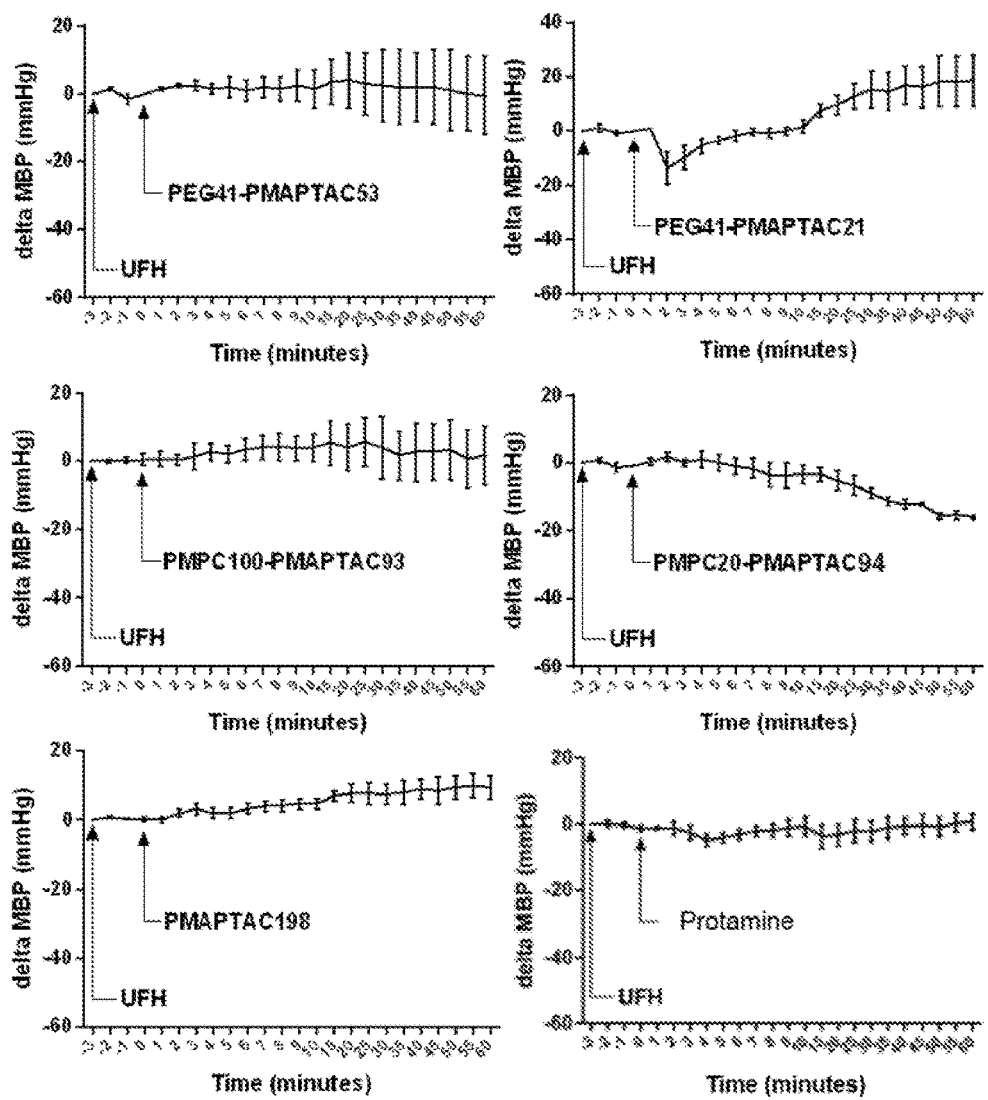

Fig. 10 The concentration changes of enoxaparin (Clexane), a LMWH, according to mass ratio of PEG41-PMAPTAC53/LMWH.
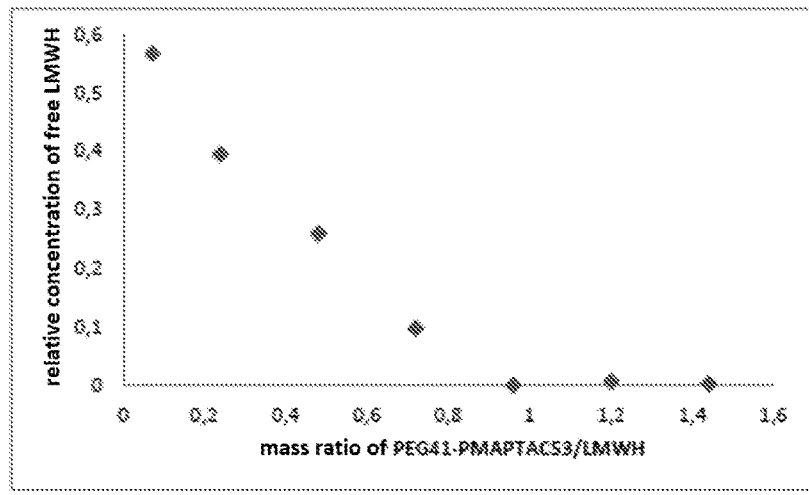
Fig. 11 Neutralization of the enhancement of anti-fXa activity induced by enoxaparin (Clexane), a LMWH, during incubation with different concentrations of PEG41-PMAPTAC53 in a 96-wells polystyrene plate.
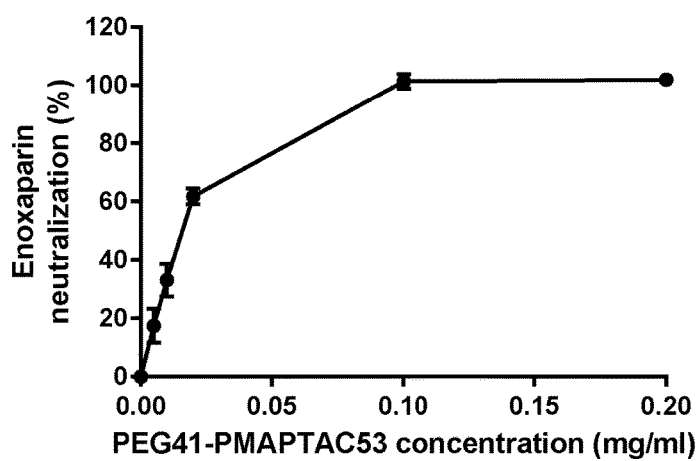

Fig. 12 Neutralization of the enhancement of ACT induced by enoxaparin (Clexane), a LMWH, after infusion of PEG41-PMAPTAC53 into rats. Mann-Whitney test. Data are expressed as mean ±SD, n = 6.
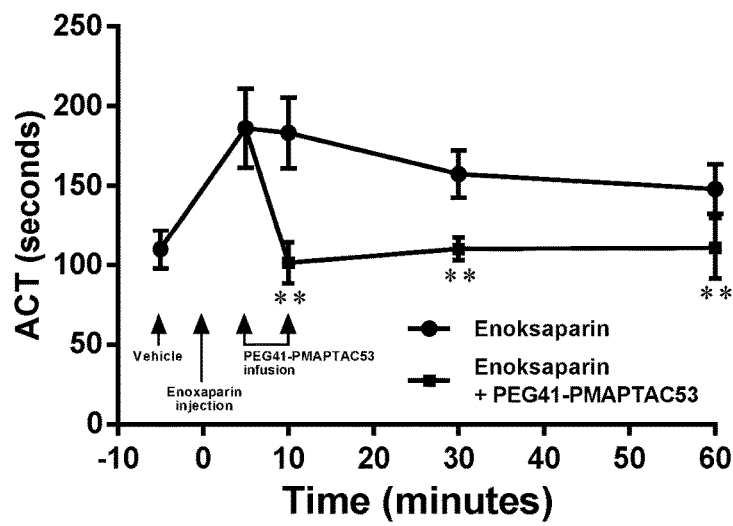
Fig. 13 The intensity of fluorescence signal from labeled PEG41-PMAPTAC53 registered intravially in mice (2A: T= 5 min; 2B: T= 15 min; 2C: T= 30 min; 2D: T=60 min; 2E: T=120 min).
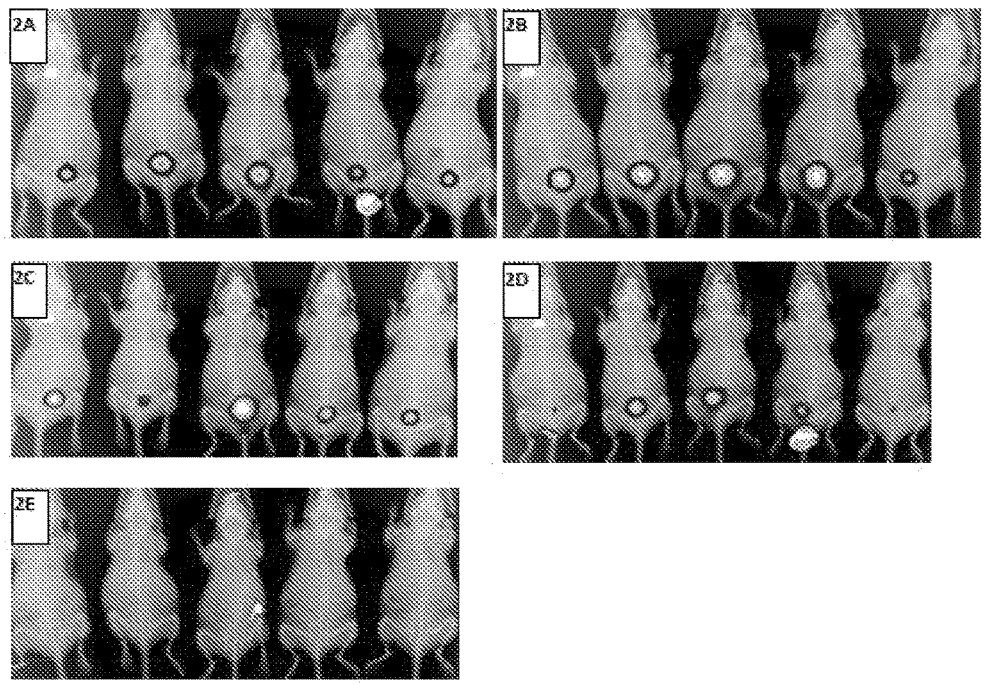

Fig.14 The intensity of fluorescence signal from labeled PEG41-PMAPTAC53 registered intravially in mice.
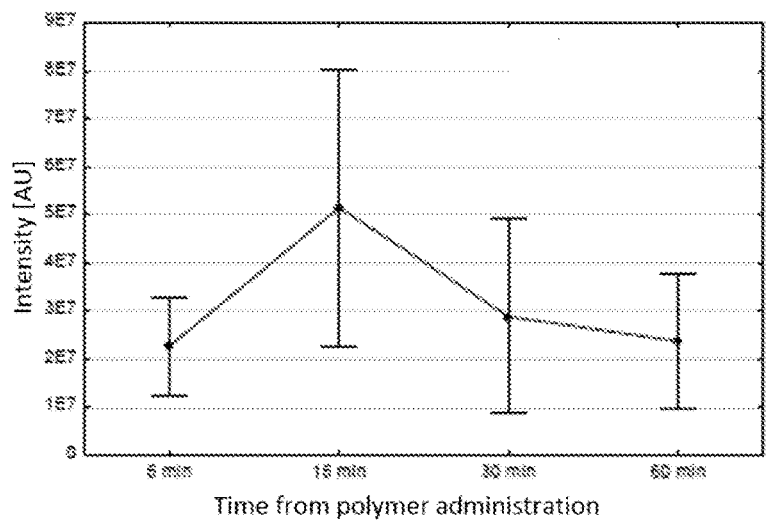
Fig.15 The intensity of fluorescence signal from labeled PEG41-PMAPTAC53 registered intravially in liver and kidneys collected from mice.
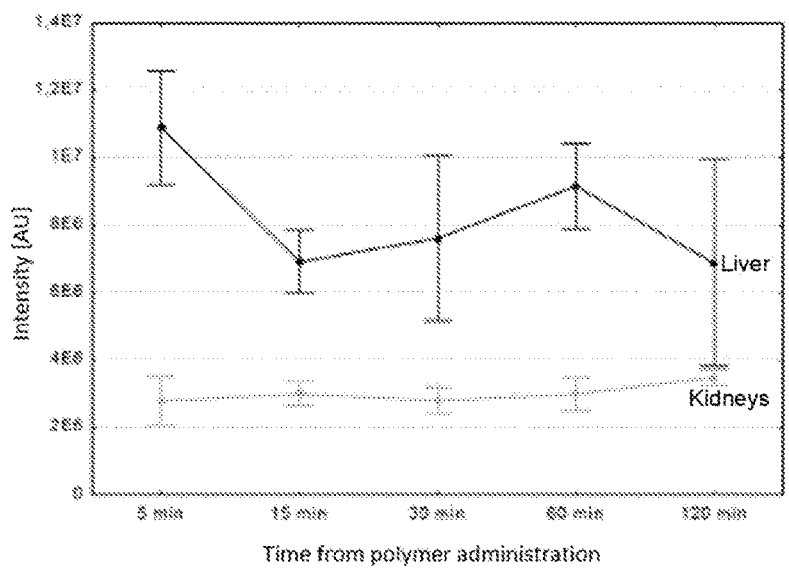

Fig. 16 Intravital fluorescence imaging of liver and kidneys collected from mice injected with labeled polymer PEG41-PMAPTAC53 in different time points (the organ located in the lower left corner of single picture is the fluorescence imaging of organ collected from animal injected with (not labeled) vehicle
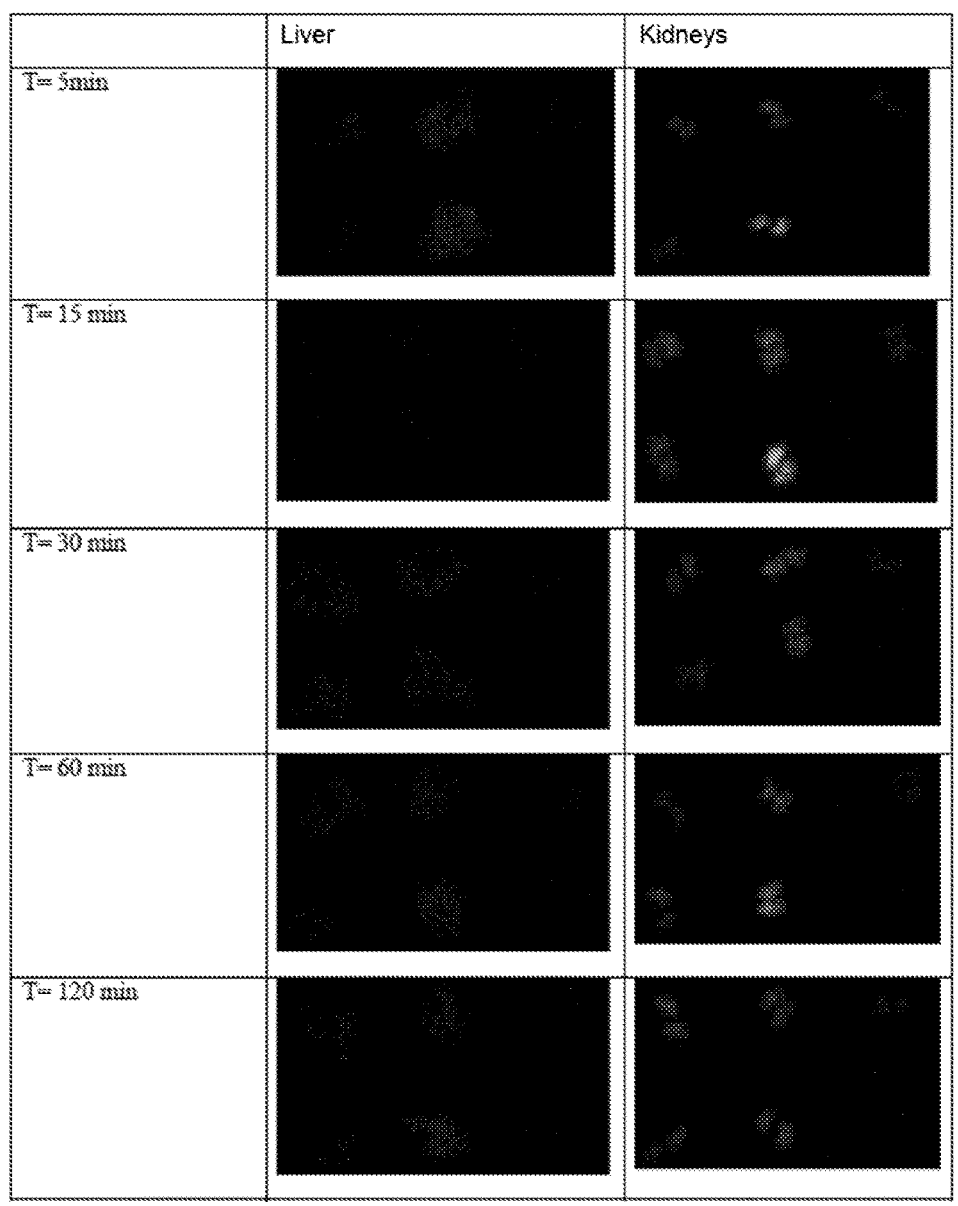

Fig. 17 Intravital fluorescence imaging of liver and kidneys collected from mice injected with labeled protamine sulfate at different time points (the organ located in the lower left corner of single picture is the fluorescence imaging of organ collected from animal injected with (not labeled) vehicle
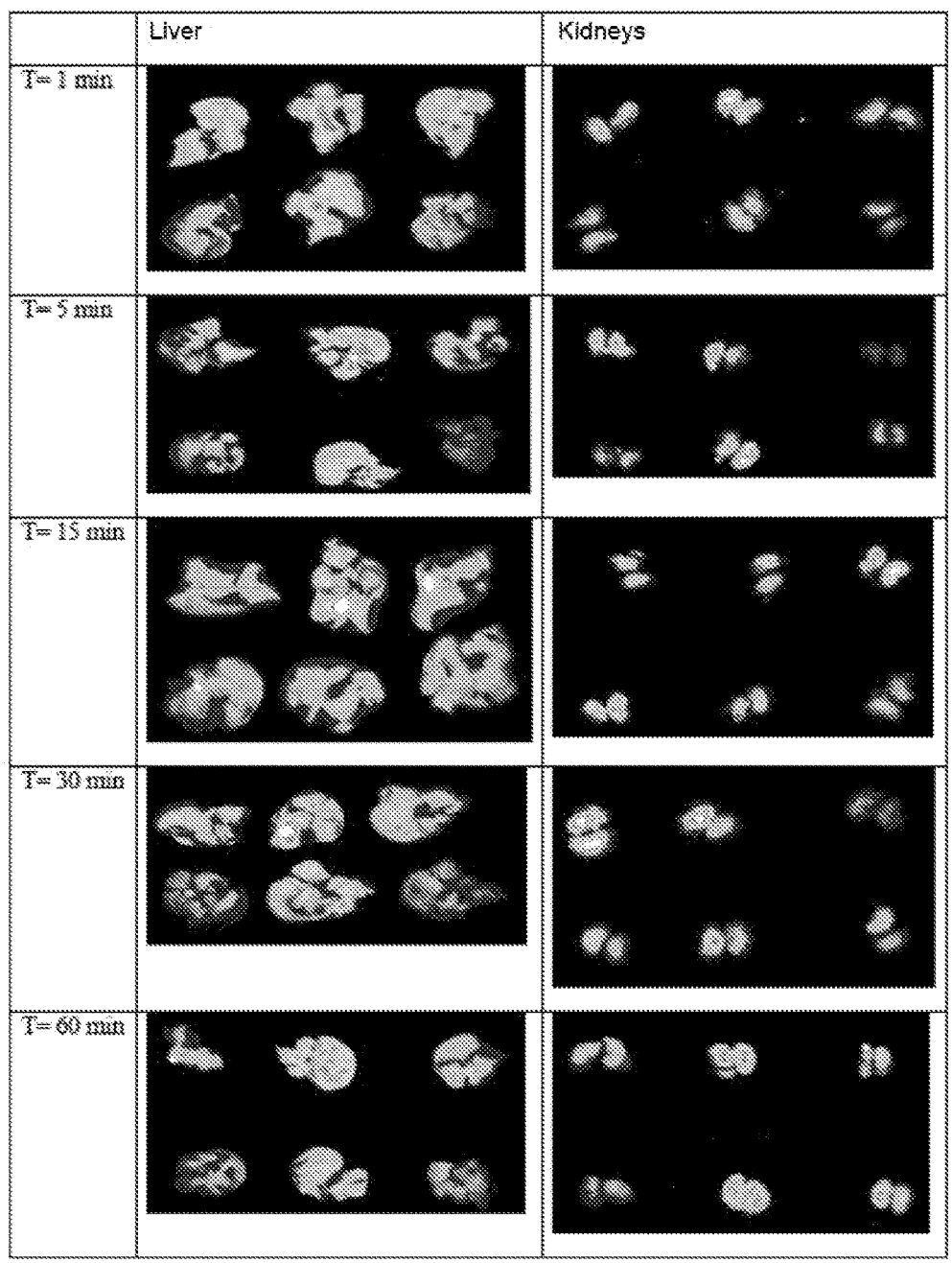

Fig.18 The intensity of fluorescence signal from rhodamine-labeled protamine sulfate registered intravially in organs collected from mice.
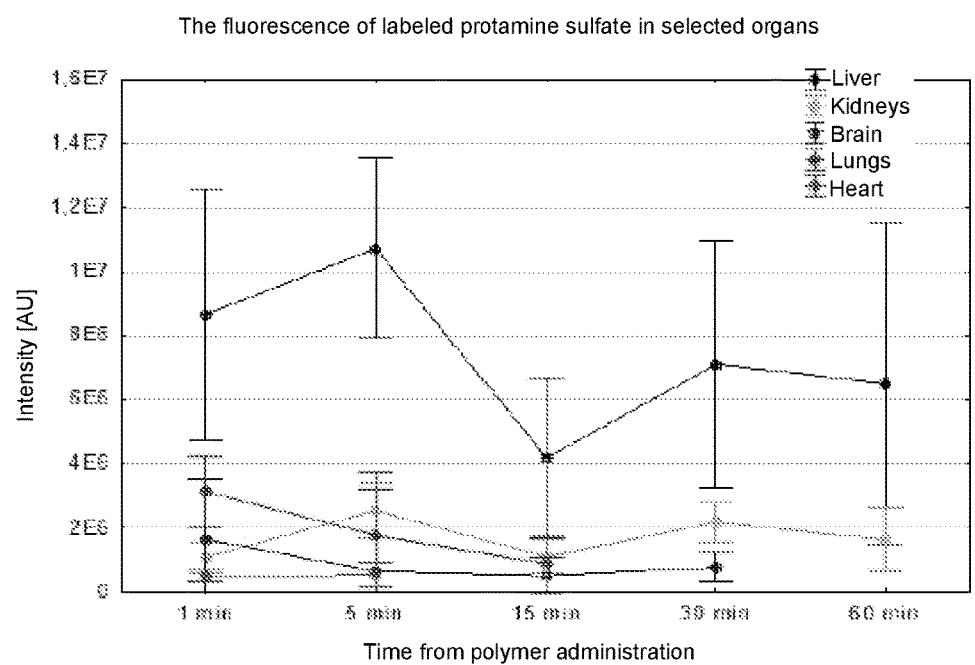

Fig.19 The changes systolic arterial blood pressure (A), heart rate (B), body temperature (C), blood oxygen saturation (D), tissue perfusion registered on rat's paw (E), peak exhaled $CO_2$ (F), and respiratory rate (G) registered for 60 min after intravenous administration of vehicle (PBS) and unfractionated heparin (UFH) in a dose of 900 IU/kg alone or UFH followed (3 minutes) by intravenous fast injection or 5-minute infusion of PEG41-PMAPTAC53 (5.85 mg/kg, C) or short-time (5 min) intravenous infusion. Results are shown as mean. n = 3-7.

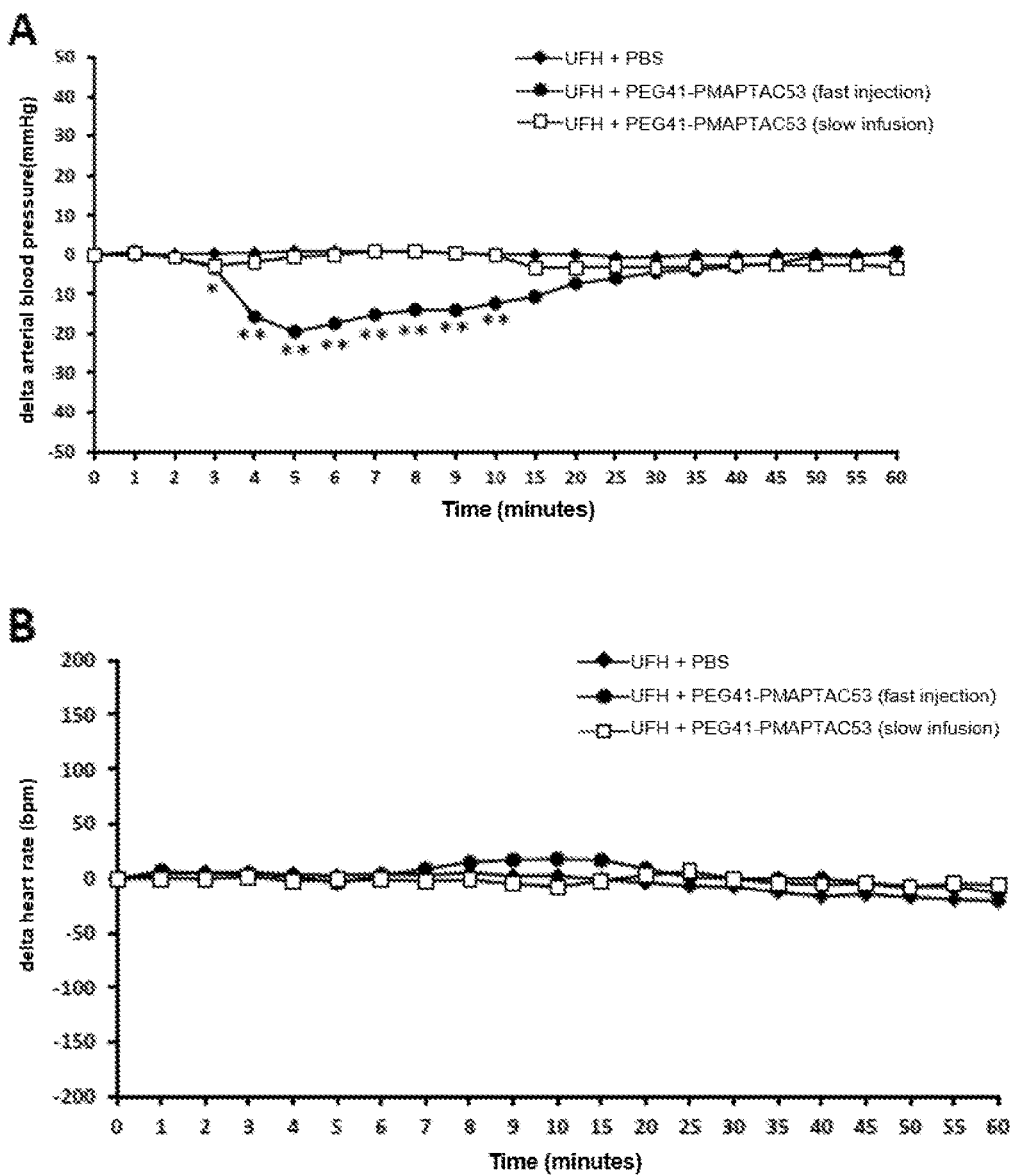

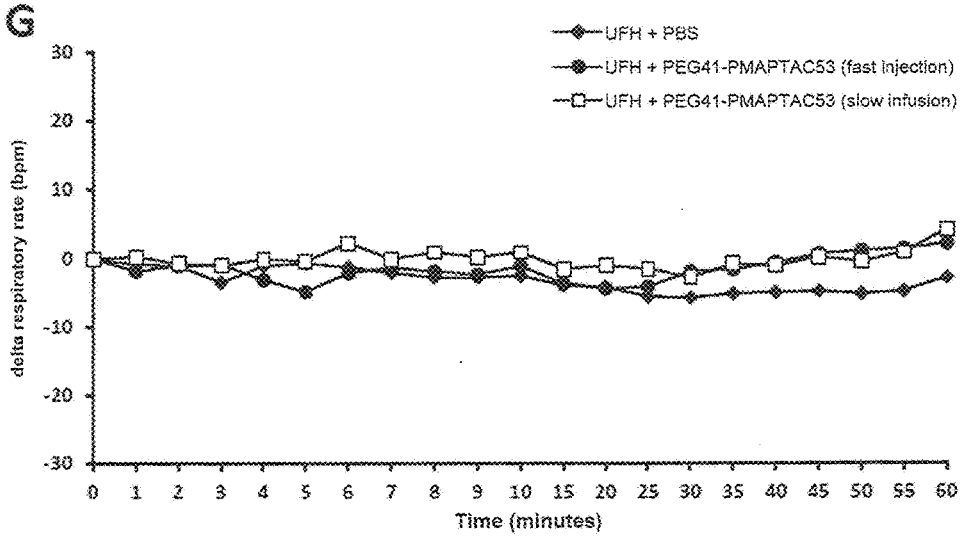

Fig. 20 The effect of polymer on hematologic parameters: WBC, RBC, HGB, HCT, MCV, MCH, MCHC, PLT measured after 30-minute incubation of polymer in a concentration of 1, 10, and 100 μg/ml. The results are presented as % changes in comparison to control group (PBS) and mean ± SD; n=3.

WBC, white blood cells; RBC, red blood cells; HGB, hemoglobin; HCT, hematocrit; MCV, mean corpuscular volume; MCH, mean corpuscular hemoglobin; MCHC, mean corpuscular hemoglobin concentration; PLT, blood platelets.

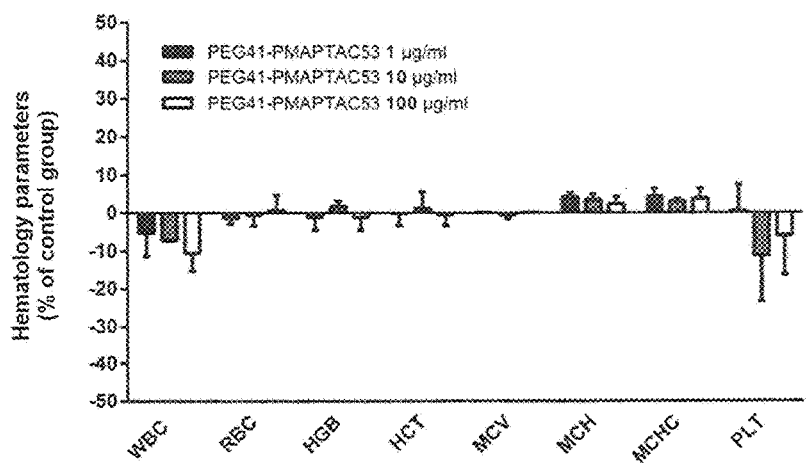

Fig.21 Hematologic parameters: WBC (A), RBC (B), HGB (C), HCT (D), MCV (E), MCH (F), MCHC (G), PLT (H) measured after 7, 14 and 28 days after treatment PBS – control group, unfractionated heparin (UFH) in a dose of 300 U/kg, or UFH followed by protamine in a dose of 3 mg/kg, or polymer in a dose of 1.95 mg/kg. The results are presented as mean ± SD; n=3-7.

WBC, white blood cells; RBC, red blood cells; HGB, hemoglobin; HCT, hematocrit; MCV, mean corpuscular volume; MCH, mean corpuscular hemoglobin; MCHC, mean corpuscular hemoglobin concentration; PLT, blood platelets.

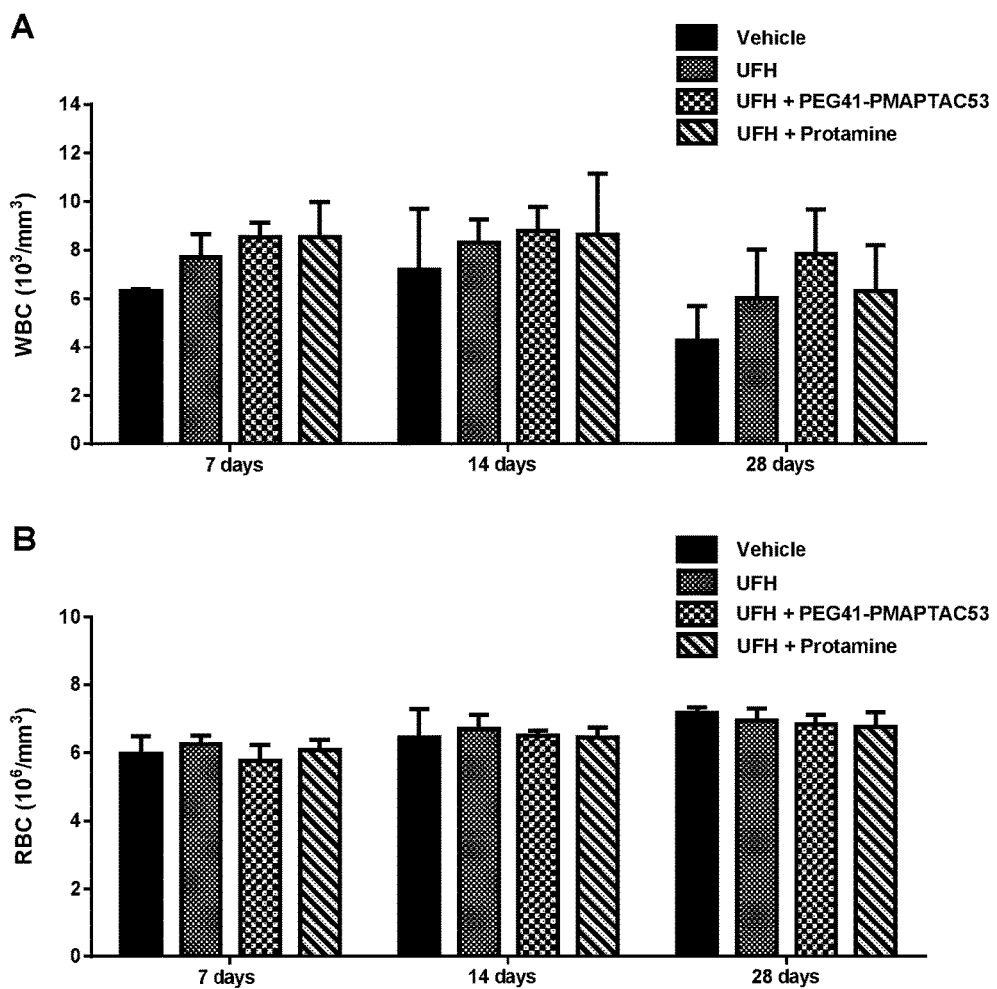

Fig.22 The effect of polymer on blood chemistry: aspartate aminotransferase (AST) (A), alanine transaminase (ALT) (B), amylase (C), alkaline phosphatase (D), creatine phosphokinase (E) 6 hours, 7, 14 and 28 days after treatment with 300 U/kg unfractionated heparin (UFH), 300 U/kg UFH + 1.95 mg/kg PEG41-PMAPTAC53 and 300 U/kg UFH + 3 mg/kg protamine.
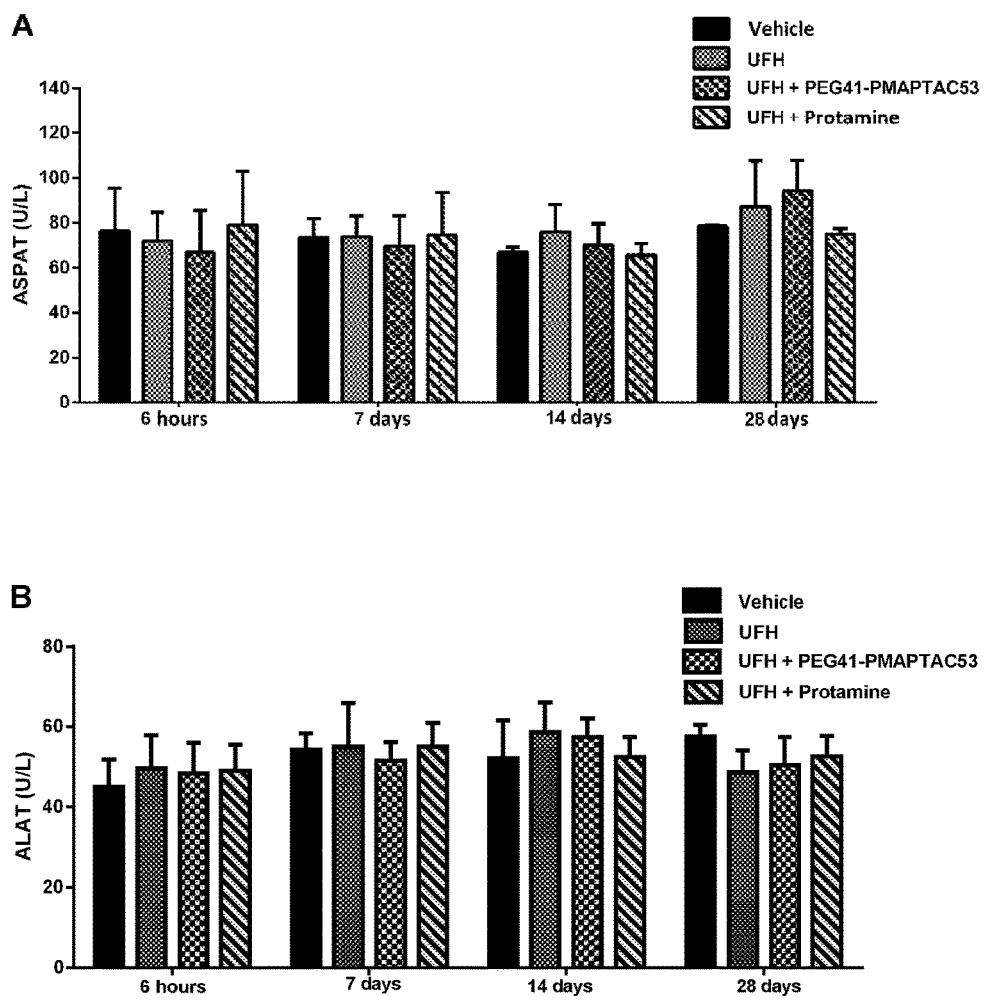

Fig. 23 Example histologic preparations of lungs and liver of rat 1 hour after treatment with PBS (A, B), unfractionated heparin (UFH) (C, D) UFH with protamine (E, F) or with PEG41-PMAPTAC53 (G, H) and 28 days after treatment with UFH with protamine (I, J) or with PEG41-PMAPTAC53 (K, L).
A. Control group (PBS) (rat) lungs after 1 hour; magnification x100
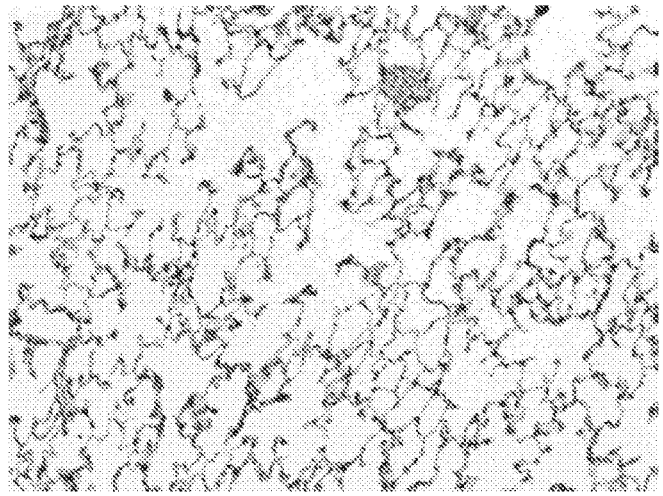
B. Control group (PBS) (rat) liver after 1 hour; magnification x100
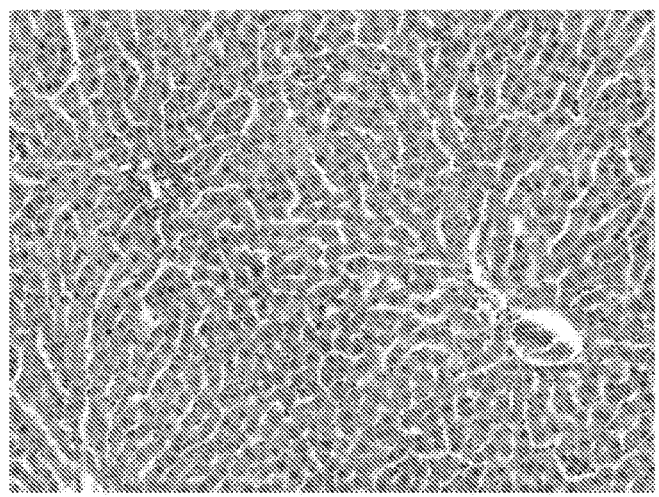

Fig. 23C. UFH (rat) lungs after 1 hour; magnification x100
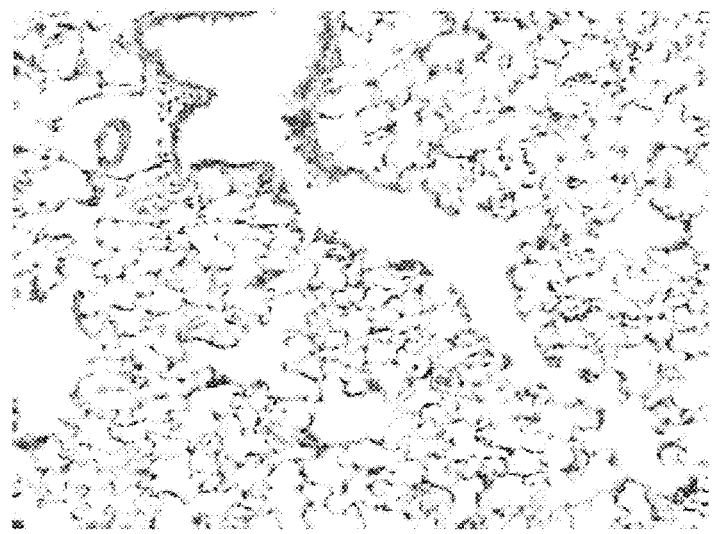
Fig. 23D. UFH (rat) liver after 1 hour; magnification x100
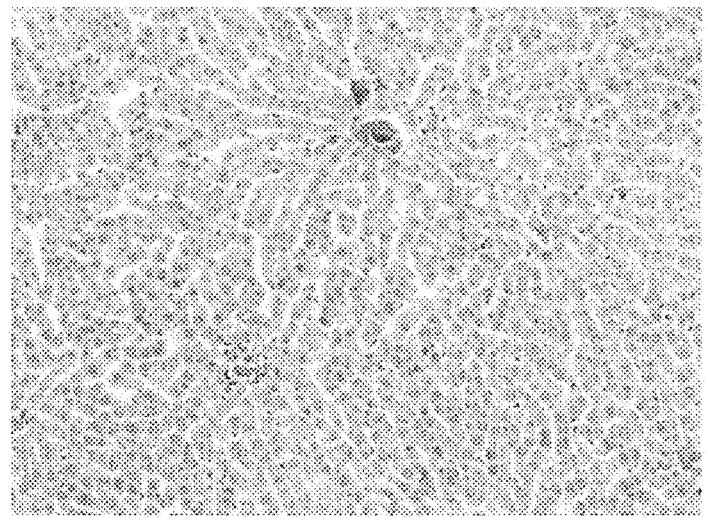

Fig. 23E. UFH + PROTAMINE (rat) lungs after 1 hour; magnification x100
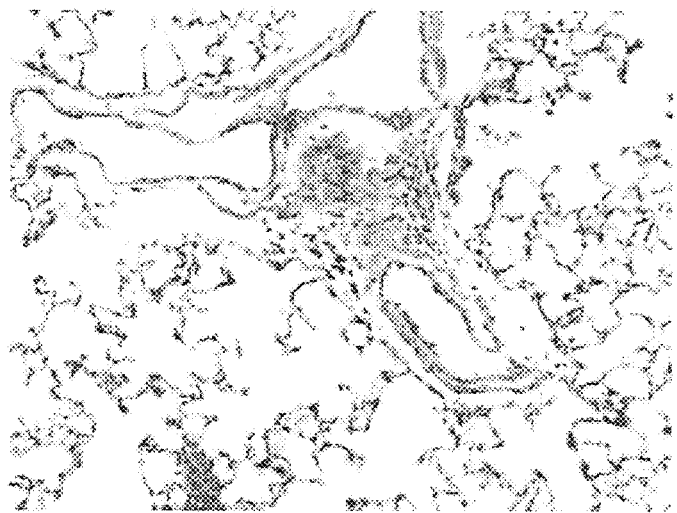
Fig. 23F. UFH + PROTAMINE (rat) liver after 1 hour; magnification x100
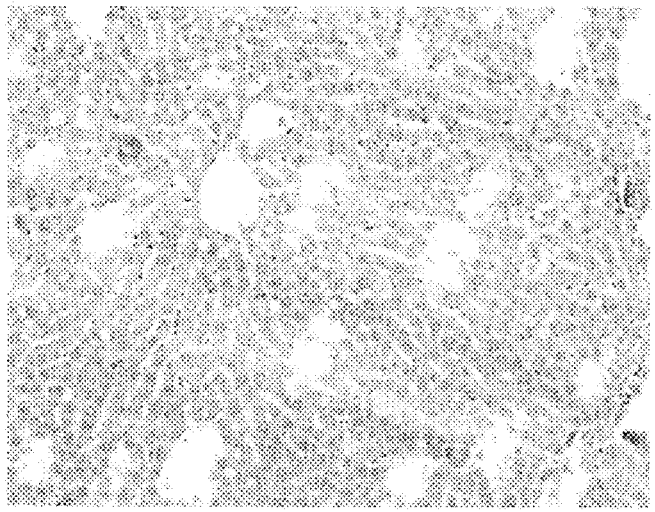

Fig. 23G. UFH + polymer PEG41-PMAPTAC53 (rat) lungs after 1 hour; magnification x100
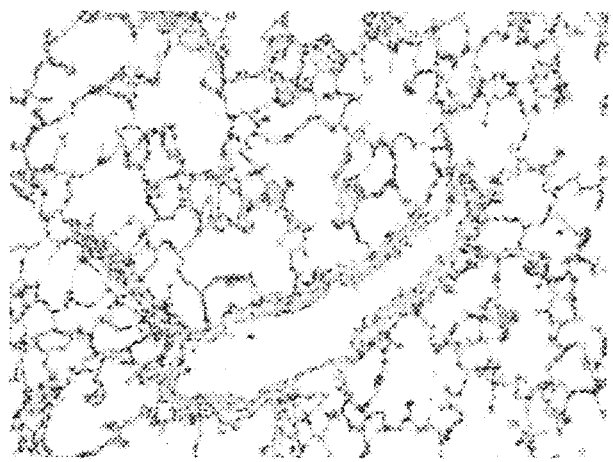
Fig. 23H. UFH + polymer PEG41-PMAPTAC53 (rat) liver after 1 hour; magnification x100
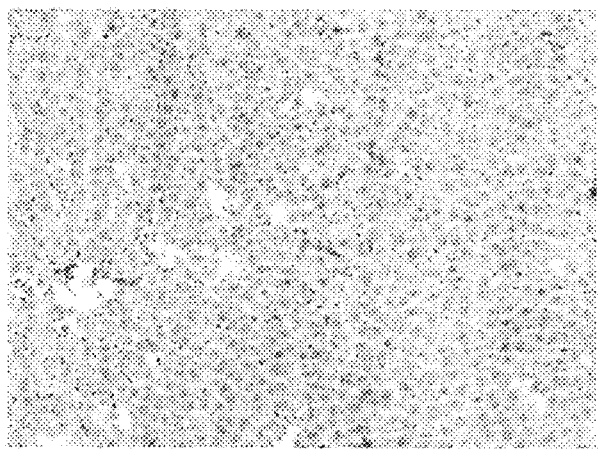

Fig. 23I. UFH + PROTAMINE (rat) lungs after 28 days; magnification x100
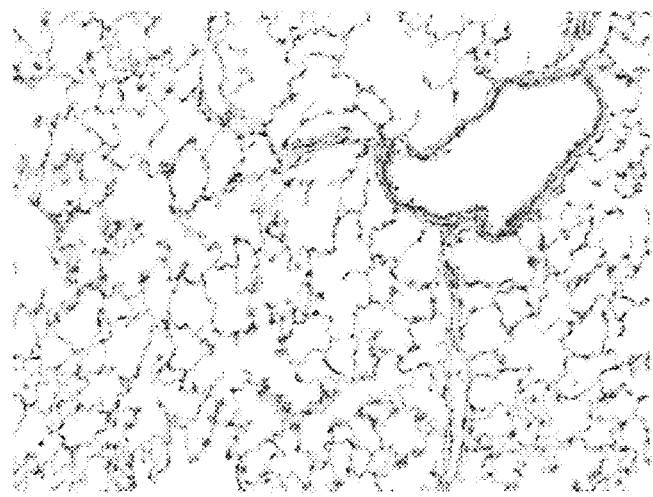
Fig. 23J. UFH + PROTAMINE (rat) liver after 28 days; magnification x100
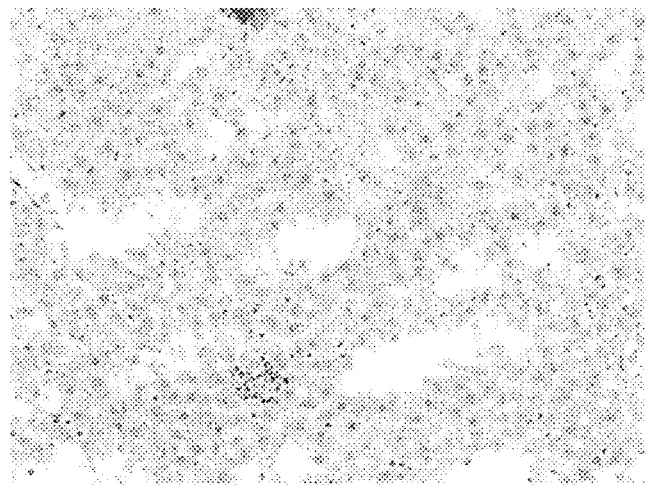

Fig. 23K. UFH + polymer PEG41-PMAPTAC53 (rat) lungs after 28 days; magnification x100
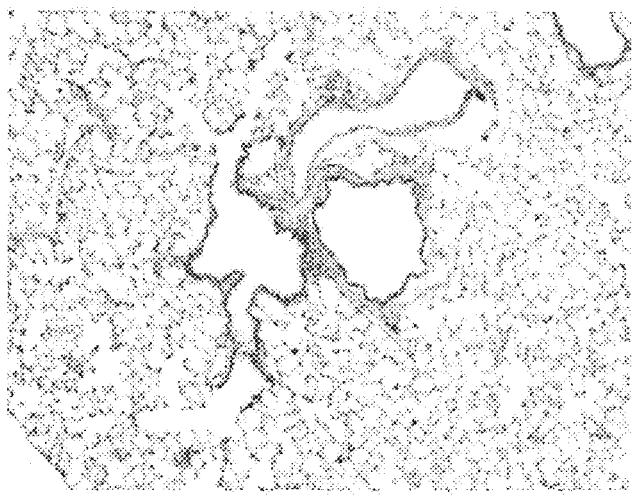
Fig. 23L. UFH + polymer PEG41-PMAPTAC53 (rat) liver after 28 days; magnification x100
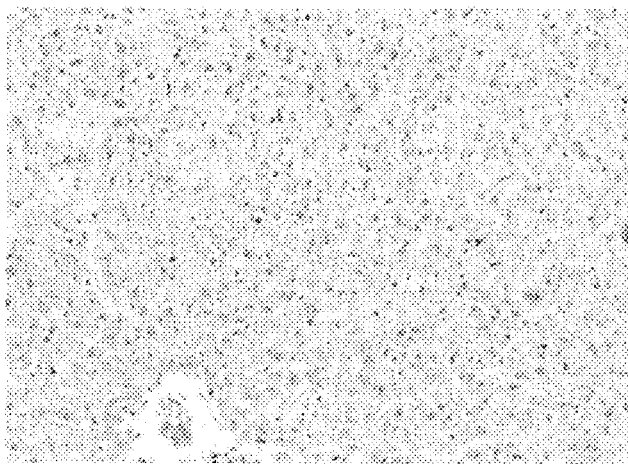

USE OF A BLOCK POLYMER COMPRISING A BLOCK OF POLY(3-(METHACRYLOYLAMINO) PROPYLTRIMETHYLAMMONIUM CHLORIDE) (PMAPTAC) FOR THE NEUTRALIZATION OF HEPARIN

CROSS-REFERENCE TO RELATED APPLICATION

This is a § 371 application of International Patent Application No. PCT/PL2016/050028, filed Jun. 9, 2016, which claims benefit of Polish Patent Application No. P.412654, filed Jun. 10, 2015, and which is incorporated herein by reference.

TECHNICAL FIELD

The subject of the invention is the use of block polymers for heparin neutralization.

BACKGROUND OF INVENTION

Heparin, a substance discovered by McLean at the beginning of the XX century, is applied in clinics since 1937 and is the first polysaccharide-based drug included in the WHO list of essential medicines. Heparin is a glycosaminoglycan (GAG) with a large molecular weight dispersity and high degree of substitution with sulfate groups (it has the largest density of a negative charge among biomolecules reaching 2.7 charges per a repeat unit consisting of a glucosamine group and an L-iduronic acid group). Heparin is produced and stored in mast cells, macrophages and in the vascular endothelium. It is obtained from the animal tissues, particularly from porcine intestines and bovine lungs. It shows very strong inhibition of blood coagulation, although only one third of heparin molecules show anticoagulative properties. Its action is based on enhancing the ability of antithrombin (AT) to deactivate thrombin and Xa factor, the enzymes responsible for the production of fibrin during clot formation. Heparin is a drug of choice in the situations when fast inhibition of coagulation is necessary, e.g. during surgical operations, in particular to prevent formation of clots in the apparatus used in extracorporeal circulation, such as dialyzers or oxygenators. It also has many other therapeutic applications, e.g., in the treatment of unstable angina pectoris or acute heart infarction. It may also lower cholesterol and lipids. Two laboratory tests are used to assess the activity of heparin, i.e., activated partial thromboplastin time (aPTT) and activated clotting time (ACT). The former is used for more precise monitoring of lower doses and is applied rather in prophylaxis while the latter is used to monitor general heparin activity in a wide range of doses and is used during surgical operations.

However, the application of heparin is connected with many adverse effects, among which the most frequent ones are hemorrhages, heparin induced thrombocytopenia (HIT), hypercalcemia which results in osteoporosis on prolonged administration of heparin and increased aminotransferase level in blood. In order to prevent the adverse effects of lowered coagulation it is often necessary to neutralize or remove heparin from blood after an expected anticoagulation effect is reached. Also, because of the adverse effects of heparin, low molecular weight heparins (LMWH) are more and more frequently used, which due to shorter chains show mainly anti-Xa activity. Due to the differences in the mechanism of action these drugs are safer and show prolonged action therefore they may be chronically applied. Their drawback is that they have no effective antidote and when overdosed it is more difficult to return normal blood coagulation in a patient. When it is necessary to assess their anticoagulative action, the activity against the active Xa factor (anti-Xa activity) is evaluated.

In the current state of art the only clinically used drug neutralizing heparin action is protamine, a protein which was introduced to clinical application almost simultaneously with heparin (Fischer, A Biochem Zeit. 278, 133, 1935.). It possesses exceptionally high content of basic amino acids such as arginine, lysine, and histidine, which may reach 80%. Another polymer which was studied for heparin removal is poly-L-lysine (Ma, X., Mohammad, S. F., Kim, S. W., Biotechnology and Bioengineering, 1992, 40(4), 530-536).

Yet another approach to heparin neutralization problem is its enzymatic degradation using immobilized heparinase (Kolde, H.-J., Pelzer, H., Borzhenskaya, L., Russo, A., Rose, M., Tejidor, L. Hamostaseologie 1994, 14(1), 37-43).

Unfortunately, the mentioned methods of heparin neutralization may have adverse effects. Protamine, if not neutralized or removed from blood, may result in adverse reactions in about 10% of patients. They may be very serious and even lethal including pulmonary hypertension, arterial hypotension, anaphylactic shock, thrombocytopenia and granulocytopenia. Heparin neutralization with protamine is incomplete and is accompanied with allergic reactions.

Anticoagulative activity of low-molecular-weight heparins may be only partially neutralized (up to 60% maximum) by intravenous injection of protamine sulfate (http://products.sanofi.us/lovenox/lovenox.html). However, except for protamine there are no other compounds neutralizing these anticoagulants on the market. The introduction of a safe and efficient antidote for low-molecular-weight heparins could extend their applications with those currently typical of unfractionated heparin.

Except for chemical methods of heparin neutralization, there were also studies on the methods of its physical removal from blood.

The devices for physical heparin removal from blood were mostly based on the application of immobilized poly-L-lysine (Joseph B. Zwischenberger, MD, Roger A. Vertrees, BA, CCP, Robert L. Brunston, Jr., MD, Weike Tao, MD, Scott K. Alpard, MD, and Paul S. Brown, Jr., MD, The Journal of Thoracic and Cardiovascular Surgery 1998 Volume 115, Number 3; Zwischenberger, J. B., Tao, W., Deyo, D. J., Vertrees, R. A., Alpard, S. K., Shulman, G. Annals of Thoracic Burgery Tom 71, Issue 1, 2001, Pages 270-277). The heparin removal device (HRD) described in the above papers, was included into the blood circulation system of a patient by extracorporeal venous-venous shunt. It allowed separation of serum, which upon heparin removal through the contact with poly-L-lysine, was returned into the patient's blood. In spite of promising results the experiments with the application of the devices of this type are limited and so far none of them has been introduced into clinical practice.

The method frequently used in order to avoid complications resulting from unbound heparin antagonists is their immobilization on polymeric supports in the heparin removal device. For example, protamine was supported on a matrix obtained by grafting an acrylic polymer onto cellulose (Hou, K. C., Roy, S., Zaniewski, R., Shumway, E. Artificial Organs 1990, 14((6), 436-442) or inside cellulose fibres (Wang, T., Byun, Y., Kim, J.-S., Liang, J., Yang, V. C. International Journal of Bio-Chromatography 2001, 6(2), 133-149). It was shown that the bioreactor removed more than 50% of administered heparin during 10 at the blood flow of 100 mL/min. The application of a bioreactor containing immobilized protamine did not result in any statistically significant changes in the monitored hemodynamic parameters.

Another paper reports efficient heparin removal using spheres obtained from alginate and poly-L-lysine (M. Sunil Varghese, D. Hildebrandt, and D. Glasser, N. J. Crowther, D. M. Rubin, Artificial Cells, Blood Substitutes, and Biotechnology, 2006, 34, 419-432). However, the polymeric spheres could not be applied in vivo.

Inventors of the present invention have previously developed heparin neutralization methods based on the application of polysaccharides in the soluble form to neutralize heparin without its physical removal from blood (patent application P 387249) or based on crosslinked polysaccharides in the form of microspheres for the neutralization of heparin in blood by its physical removal. The studies on antiheparin activity of polymers described in the present application are a continuation of the studies described in the previous applications.

The methods described above do not allow effective heparin neutralization. Protamine used commonly in clinical practice may cause serious adverse effects, while the attempts to remove heparin from blood with the methods of its physical removal were found to be uncomfortable and impractical due to the limitations in their application, including the necessity of hospitalization of the patients.

SUMMARY OF INVENTION

The aim of the invention was to provide a novel, efficient method of the neutralization of both unfractionated and low-molecular-weight heparin without adverse effects and patients discomfort.

Unexpectedly it was found that this goal may be reached via the use of synthetic block polymers.

The subject matter of the invention is to ue a block polymer containing a block of poly(3-(methacryloylamino) propyltrimethylammonium chloride) (PMAPTAC) to directly neutralize heparins in blood and physiological fluids, particularly unfractionated heparin and low-molecular-weight heparin.

The block polymers are a type of polymers, whose chains are composed of two or more blocks, which are built of different units called mers.

Methacrylic acid and its derivatives (methacrylates) are widely used to produce polymers since 30 s of XX century and the polymerization reaction of methacrylic acid is known since 1877. The scope of applications of the polymers based on methacrylates is wide ranging from organic glass (commonly known as "Plexiglass") to contact lenses and the elements of endoprostheses. The advantage of these polymers is the possibility to obtain them using different polymerization methods, including controlled radical polymerization (CRP), e.g., reversible addition-fragmentation chain transfer polymerization (RAFT) used to obtain the polymers which are the subject of the present application. CRP techniques allow preparation of polymers with a very well defined structure and molecular weight. They are particularly well suited to obtain polymers with advanced architectures such as block polymers.

2-(Methacryloyloxy)ethyl phosphorylcholine (MPC) is a zwitterionic derivative of methacrylic acid containing a group present also in lecithin, a phospholipid which is the main component of a cell membrane (Iwasaki, Y., Ishihara, K. Cell membrane-inspired phospholipid polymers for developing medical devices with excellent bio-interfaces, Science and Technology of Advanced Materials, 2012, 13(6), 064101; Ishihara, Kazuhiko, Ueda, Tomoko, Nakabayashi, Nobuo Preparation of phospholipid polymers and their properties as polymer hydrogel membranes, Polymer Journal, 1990, 22(5), 355-360). Due to this structural similarity to the components of the cell membranes the polymers based on 2-(methacryloyloxy)ethyl phosphorylcholine (MPC) are biocompatible. They are particularly often used to modify the surfaces to prevent the formation of biofilms, e.g., bacterial (Hirota K, Yumoto H, Miyamoto K, Yamamoto N, Murakami K, Hoshino Y, Matsuo T, Miyake Y. J Dent Res. 2011, 90(7), 900-5) and thrombi (O. Katakura, N. Morimoto, Y. Iwasaki, K. Akiyoshi, S. Kasugai Med Dent Sci 2005, 52, 115).

Poly(ethylene glycol) (PEG) is a polymer commonly applied as a component of cleaning agents (e.g., liquid soap) and cosmetics. It is also used in medicine to prepare molecular masking systems decreasing the interaction of micro- and nanoobjects in living organisms. For example, proteins with attached PEG chain do not activate the immunological system. Thanks to its biocompatibility PEG also improves biological parameters of macromolecules to which it is attached (Kreppel, Florian; Kochanek, Stefan, Molecular Therapy 2007, 16(1), 16-29).

The solution according to the invention is preferably based on the use for the direct neutralization of heparins in blood and physiological fluids, particularly unfractionated heparin or low-molecular-weight heparin, of PEG-PMAPTAC copolymer (a block polymer containing poly(ethylene glycol) (PEG) block and a block of poly(3-(methacryloylamino)propyltrimethylammonium chloride)), most preferably PEG41-PMAPTAC53 or PEG41-PMAPTAC21, as a PMAPTAC-containing block copolymer Preferably, the solution according to the invention involves the application of a PMPC-PMAPTAC copolymer (block copolymer containing a block of 2-(methacryloyloxy)ethyl phosphorylcholine (PMPC) and a block of poly (3-(methacryloylamino)propyltrimethylammonium chloride)), most preferably PMPC20-PMAPTAC94 or PMPC100-PMAPTAC93 as a block polymer containing PMAPTAC block.

Preferably, the solution according to the invention involves the application of block polymers containing PMAPTAC obtained using the controlled radical polymerization method (CRP) for the direct neutralization in blood and physiological fluids of heparins, particularly unfractionated heparin and low-molecular-weight heparin.

The synthetic block polymers obtained using the controlled radical polymerization method (CRP) according to the invention are much better defined than the previous materials based on the natural polymers (chitosan, hydroxypropylcellulose, dextran) and their synthesis is more reproducible and independent on the natural factors. The use of the polymers according to the invention for the neutralization of heparin is also independent on the natural factors such as the fishing areas of salmon, whose sperm is used to obtain protamine, thereby significantly increasing the availability of the therapy for the patients, who require the administration of the antiheparin drugs.

Particularly preferably, the copolymer containing 41 repeating units in the PEG block and 53 repeating units in the PMAPTAC block (PEG41-PMAPTAC53) or the copolymer containing 41 repeating units in the PEG block and 21 repeating units in the PMAPTAC block (PEG41-PMAP- TAC21) are used as the PEG-PMAPTAC copolymers for direct neutralization of heparins in blood and physiological fluids.

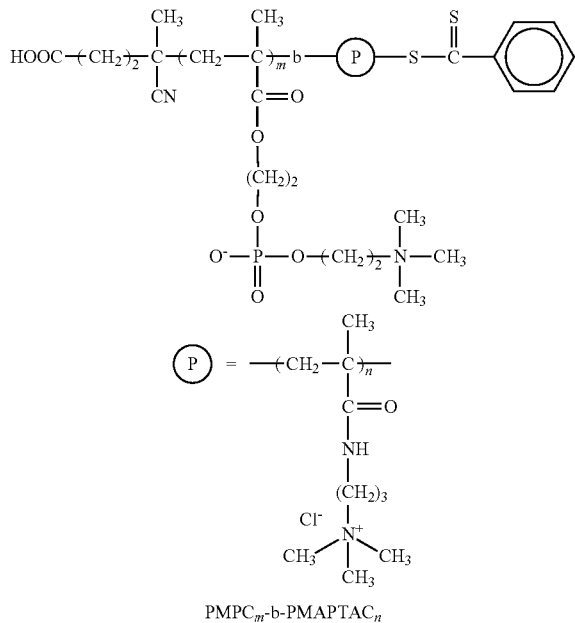

Structure of PMPC-PMAPTAC Polymers

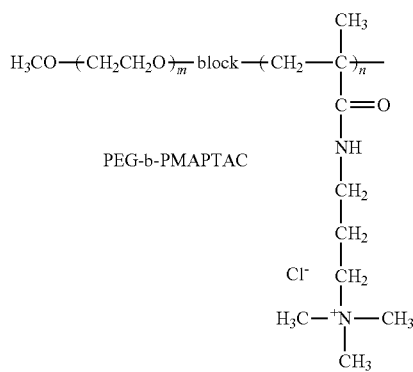

Structure of PEG-PMAPTAC Polymers

Synthetic polymers used for the neutralization of heparin have very well defined parameters and characteristics which can be controlled during polymerization and therefore allow repeatability of the neutralization process. Thus, the use of the invention eliminates the problem related to the neutralization of heparin with natural polymers.

Moreover, by using block polymers containing PEG and PMAPTAC (PEG-PMAPTAC) as well as PMPC and PMAPTAC (PMPC-PMAPTAC) for the neutralization of the anticoagulative action of heparin in blood and physiological fluids one can also neutralize low molecular weight heparins (LMWH), which cannot be achieved with the application of protamine and the materials developed earlier based on the natural polymers

BRIEF DESCRIPTION OF THE DRAWINGS

The invention is presented in figures, where:

FIG. 1 shows the dependence of the concentration of free (uncomplexed) UFH on the polymer/UFH mass ratio FIG. 2 shows the DLS results of the measurements of the size of the complexes formed by the polymers and UFH FIG. 3 shows the DLS results of the measurements of the size of the complexes formed by the polymers and protamine with bovine serum albumin FIG. 4 shows the mass of the thrombus isolated from the carotid artery of a rat with experimentally-induced thrombosis after intravenous administration of PBS buffer (control), 300 U/kg unfractionated heparin (UFH), 300 U/kg UFH+1.95 mg/kg PEG41-PMAPTAC53, 300 U/kg UFH+ 9.36 mg/kg PEG41-PMAPTAC21, 300 U/kg UFH+7.74 mg/kg PMPC100-PMAPTAC93, 300 U/kg UFH+2.25 mg/kg PMPC20-PMAPTAC94, 300 U/kg UFH+1.8 mg/kg PMAPTAC198, 300 U/kg+7.5 mg/kg Dex40-GTMAC3 and 300 U/kg UFH+3 mg/kg protamine, *** $P<0.001$ vs. control; ^ $P<0.05$, ^^ $P<0.01$, ^^^ $P<0.001$ vs. UFH. Data are shown as averages±SEM.

FIG. 5 shows the tail bleeding time in rats with experimentally-induced thrombosis after intravenous administration of PBS buffer (control), 300 U/kg unfractionated heparin (UFH), 300 U/kg UFH+1.95 mg/kg PEG41-PMAPTAC53, 300 U/kg UFH+9.36 mg/kg PEG41-PMAPTAC21, 300 U/kg UFH+7.74 mg/kg PMPC100-PMAPTAC93, 300 U/kg UFH+2.25 mg/kg PMPC20-PMAPTAC94, 300 U/kg UFH+1.8 mg/kg PMAPTAC198, 300 U/kg+7.5 mg/kg Dex40-GTMAC3 and 300 U/kg UFH+3 mg/kg protamine, *** $P<0.001$ vs. control; ^^ $P<0.01$, ^^^ $P<0.001$ vs. UFH. Data are shown as averages±SEM.

FIG. 6 shows activated partial thromboplastin time (aPTT) of the plasma taken from rats with experimentally-induced thrombosis after intravenous administration of the PBS buffer (control), 300 U/kg unfractionated heparin (UFH), 300 U/kg UFH+1.95 mg/kg PEG41-PMAPTAC53, 300 U/kg UFH+9.36 mg/kg PEG41-PMAPTAC21, 300 U/kg UFH+7.74 mg/kg PMPC100-PMAPTAC93, 300 U/kg UFH+2.25 mg/kg PMPC20-PMAPTAC94, 300 U/kg UFH+ 1.8 mg/kg PMAPTAC198, 300 U/kg+7.5 mg/kg Dex40-GTMAC3 and 300 U/kg UFH+3 mg/kg protamine, *** $P<0.001$ vs. control; ^^ $P<0.01$, ^^^ $P<0.001$ vs. UFH. Data are shown as averages±SEM.

FIG. 7 shows anti-fXa activity of the plasma taken from rats with experimentally-induced thrombosis after intravenous administration of the PBS buffer (control), 300 U/kg unfractionated heparin (UFH), 300 U/kg UFH+1.95 mg/kg PEG41-PMAPTAC53, 300 U/kg UFH+9.36 mg/kg PEG41-PMAPTAC21, 300 U/kg UFH+7.74 mg/kg PMPC100-PMAPTAC93, 300 U/kg UFH+2.25 mg/kg PMPC20-PMAPTAC94, 300 U/kg UFH+1.8 mg/kg PMAPTAC198, 300 U/kg+7.5 mg/kg Dex40-GTMAC3 and 300 U/kg UFH+3 mg/kg protamine, *** $P<0.001$ vs. control; ^^ $P<0.01$, ^^^ $P<0.001$ vs. UFH. Data are shown as averages±SEM.

FIG. 8 shows the blood parameters: WBC (A), RBC (B), HGB (C), HCT (D), MCV (E), MCH (F), MCHC (G), PLT (H) determined 1 hour after PBS administration—control group, unfractionated heparin alone (UFH) in dose 300 U/kg, or 300 U/kg UFH+1.95 mg/kg PEG41-PMAPTAC53, 300 U/kg UFH+9.36 mg/kg PEG41-PMAPTAC21, 300 U/kg UFH+7.74 mg/kg PMPC100-PMAPTAC93, 300 U/kg UFH+2.25 mg/kg PMPC20-PMAPTAC94, 300 U/kg UFH+ 1.8 mg/kg PMAPTAC198 or 300 U/kg+3 mg protamine.

Figure 19C:
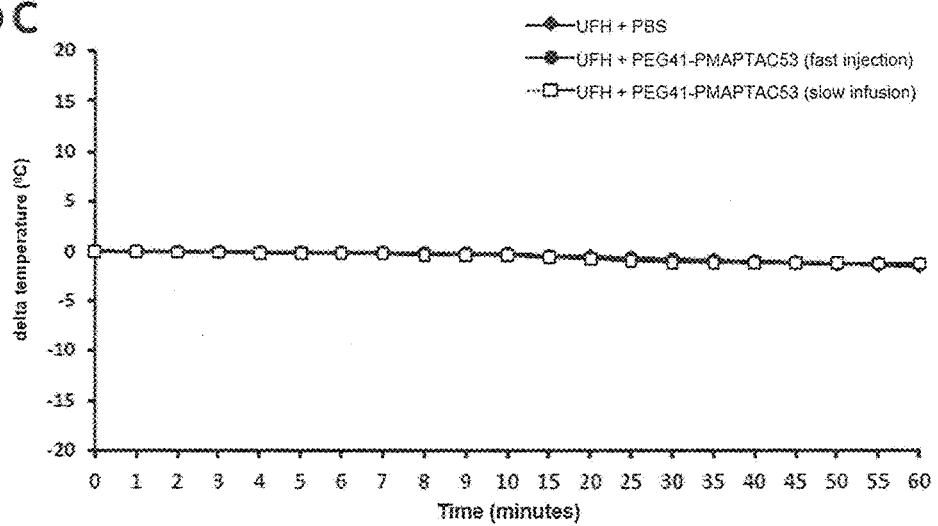
Figure 19D:
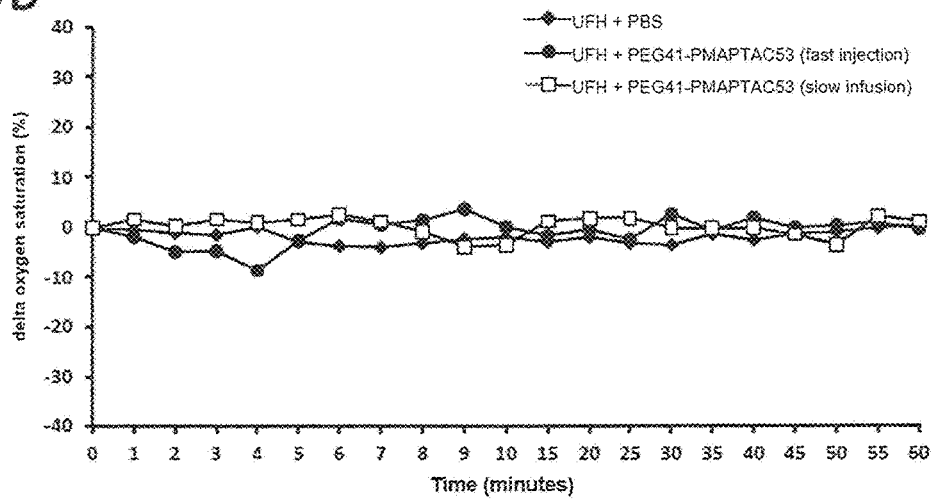
Figure 19E:
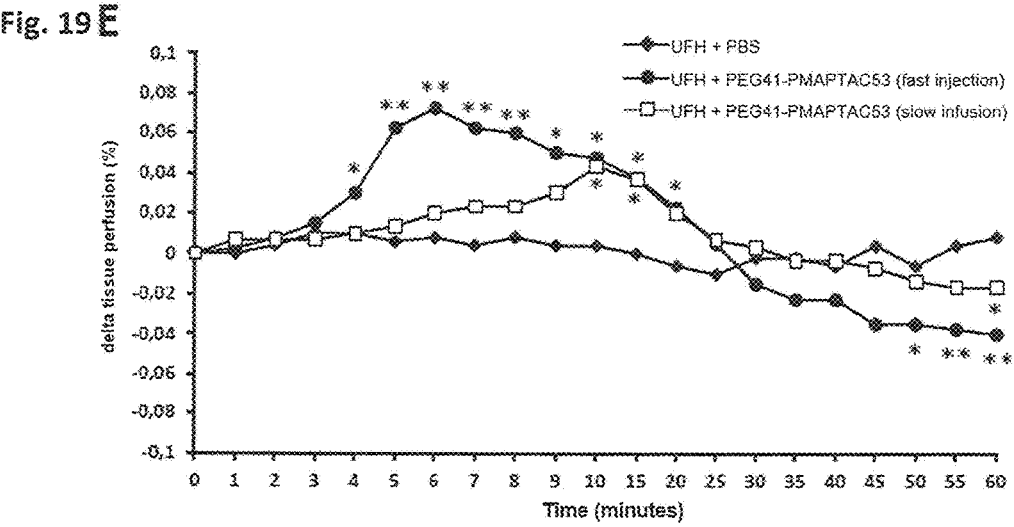
Figure 19F:
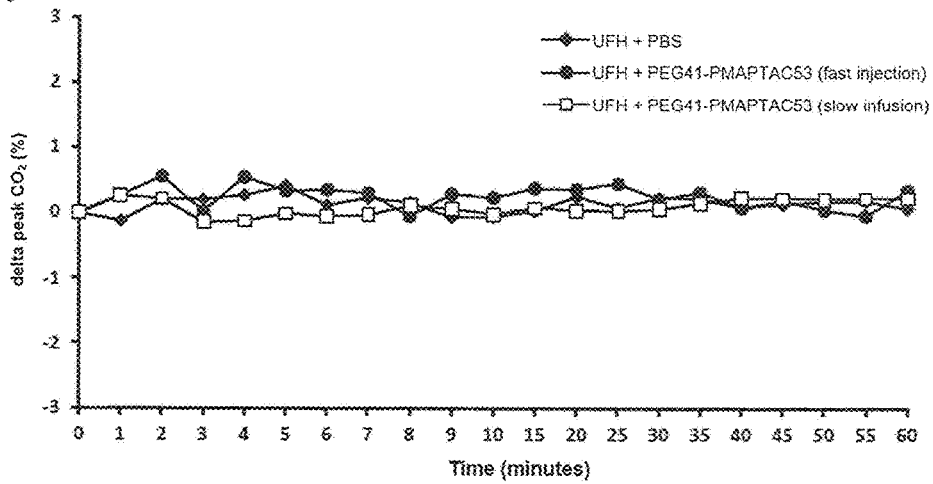

The results are shown as averages±SD; n=3-7. WBC: white blood cell count, RBC: red blood cell count, HGB: hemoglobin concentration, HCT: hematocrit, MCV: mean corpuscular volume, MCH: mean corpuscular hemoglobin, MCHC: mean corpuscular hemoglobin concentration, PLT: platelets.

FIG. 9 shows the influence of the polymers on mean blood pressure (MBP) 1 hour after administration of 300 U/kg unfractionated heparin (UFH)+1.95 mg/kg PEG41-PMAPTAC53, 300 U/kg UFH+9.36 mg/kg PEG41-PMAPTAC21, 300 U/kg UFH+7.74 mg/kg PMPC100-PMAPTAC93, 300 U/kg UFH+2.25 mg/kg PMPC20-PMAPTAC94, 300 U/kg UFH+1.8 mg/kg PMAPTAC198 and 300 U/kg UFH+3 mg/kg protamine.

FIG. 10 shows the dependence of LMWH (Clexane) concentration on PEG41-PMAPTAC53/LMWH mass ratio.

FIG. 11 shows the neutralization of anti-fXa activity of LMWH incubated with different concentrations of PEG41-PMAPTAC53 in a 96-well polystyrene plate.

FIG. 12 shows the neutralization of ACT increase induced by LMWH after administration of PEG41-PMAPTAC53 polymer to rats. Mann-Whitney test. Data are shown as averages±SD, n=6.

FIG. 13 shows the fluorescence intensity of a fluorescence label attached to PEG41-PMAPTAC53 observed during intravital imagining (2A: T=5 min; 2B: T=15 min; 2C: T=30 min; 2D: T=60 min; 2E: T=120 min).

FIG. 14 shows the intensity of the fluorescence signal of a label attached to PEG41-PMAPTAC53 polymer observed during intravital imaging.

FIG. 15 shows the intensity of the fluorescence signal of a label attached to PEG41-PMAPTAC53 polymer observed from isolated liver and kidneys.

FIG. 16 shows the fluorescence image of a liver and kidneys taken from experimental mice which were administered PEG41-PMAPTAC53 after different times (the organ in the lower left corner of the photo is a fluorescence image of an organ of an animal which was not administered the fluorescently-labeled polymer).

FIG. 17 shows the fluorescence image of a liver and kidneys taken from the experimental mice which received protamine sulfate after different times (the organ in the lower left corner of the photo is a fluorescence image of an organ of an animal which was not administered the fluorescently-labeled polymer).

FIG. 18 shows the fluorescence intensity of a label attached to protamine sulfate labeled with rhodamine observed from isolated organs.

FIG. 19 shows the change in arterial blood pressure (A), heart rate (B), body temperature (C), blood oxygen saturation (D), peripheral tissue perfusion (E), peak exhaled $CO_2$ (F) and respiratory rate (G) measured one hour after administration of unfractionated heparin (UFH) alone to rats 900 U/kg and PBS, or UFH, followed after 3 minutes by PEG41-PMAPTAC53 administration as a single injection or 5-minute infusion. Data are shown as averages, n=3-7.

FIG. 20 shows the influence of the polymer on blood parameters: WBC, RBC, HGB, HCT, MCV, MCH, MCHC, PLT determined 30 minutes after incubation of the polymer at 1, 10, 100 μg/ml. The results are shown as percent of the control group (PBS). Average±SD; n=3.

WBC: white blood cell count, RBC: red blood cell count, HGB: hemoglobin concentration, HCT: hematocrit, MCV: mean corpuscular volume, MCH: mean corpuscular hemoglobin, MCHC: mean corpuscular hemoglobin concentration, PLT: platelets.

Figure 21:
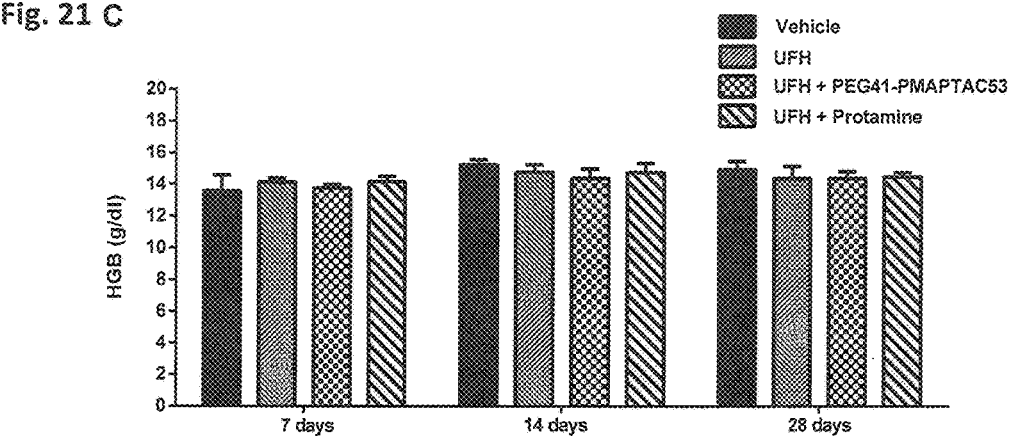
Figure 21:
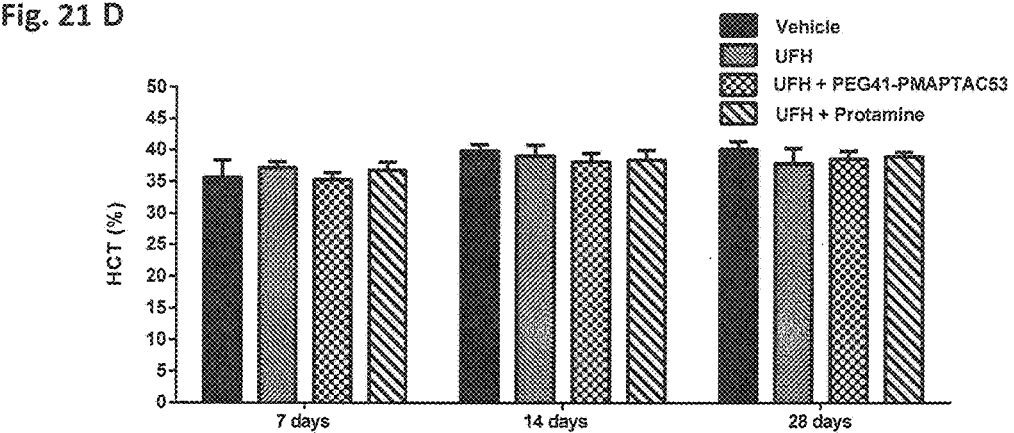
Figure 21:
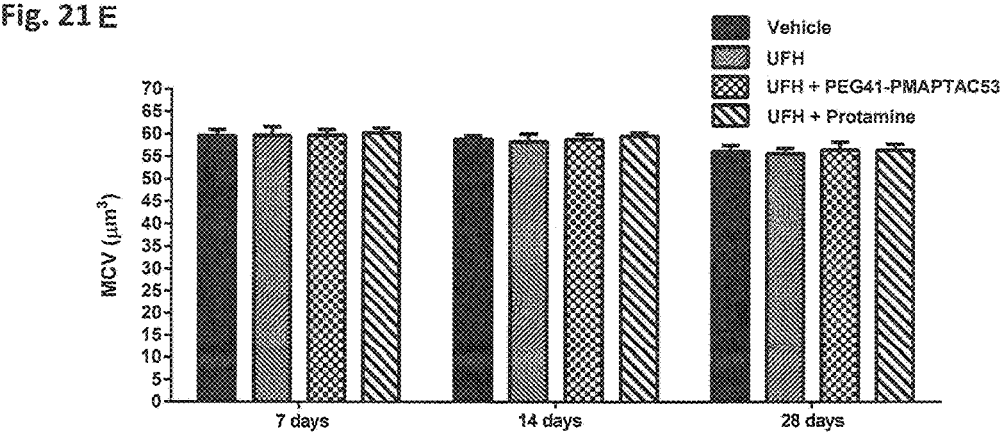
Figure 21:
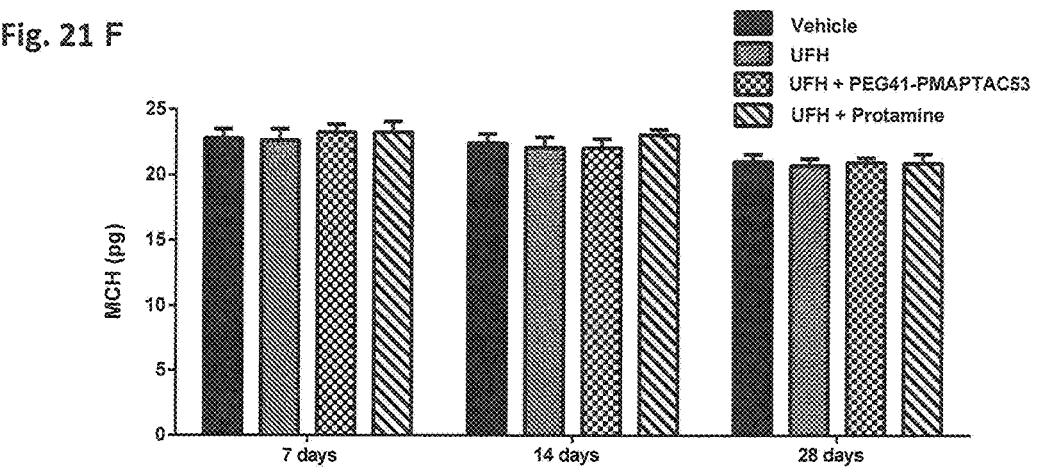
Figure 21:
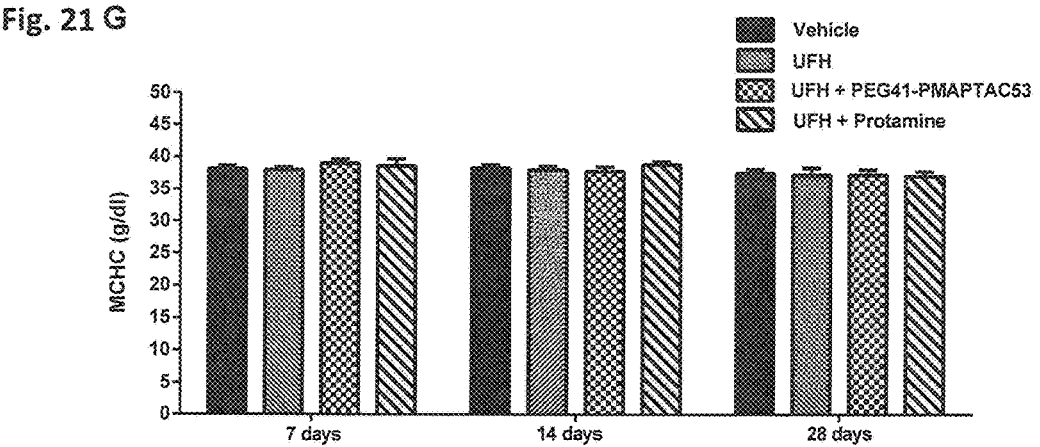
Figure 21:
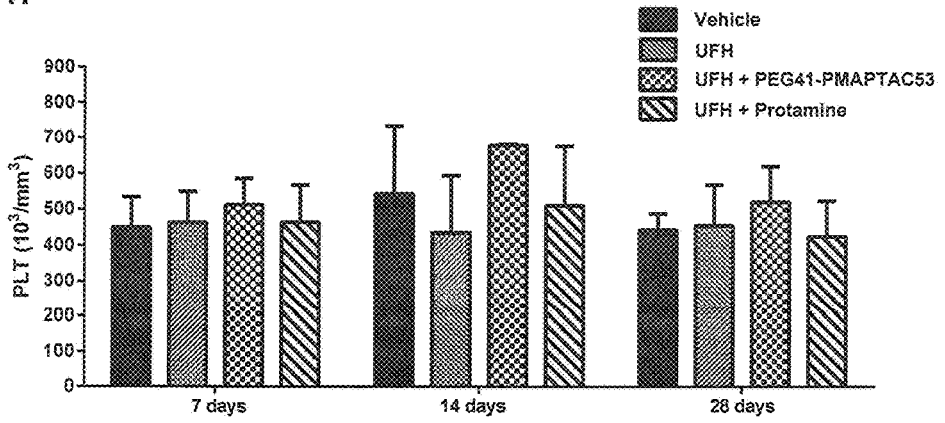

FIG. 21 shows the blood parameters: WBC (A), RBC (B), HGB (C), HCT (D), MCV (E), MCH (F), MCHC (G), PLT (H) determined 7, 14 and 28 days after administration of PBS—control group, unfractionated heparin (UFH) alone at 300 U/kg, or UFH followed by protamine 3 mg/kg, or polymer 1.95 mg/kg. The results are given as averages±SD; n=3-7.

WBC: white blood cell count, RBC: red blood cell count, HGB: hemoglobin concentration, HCT: hematocrit, MCV: mean corpuscular volume, MCH: mean corpuscular hemoglobin, MCHC: mean corpuscular hemoglobin concentration, PLT: platelets.

Figure 22:
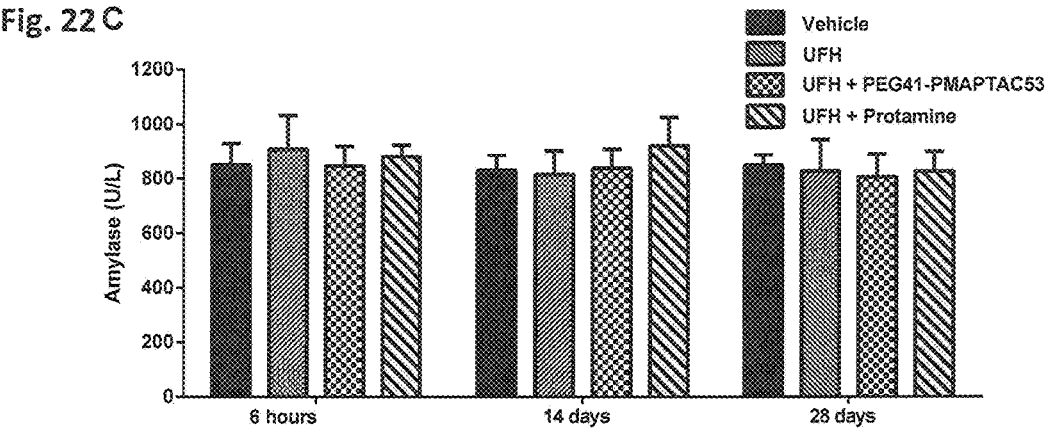
Figure 22:
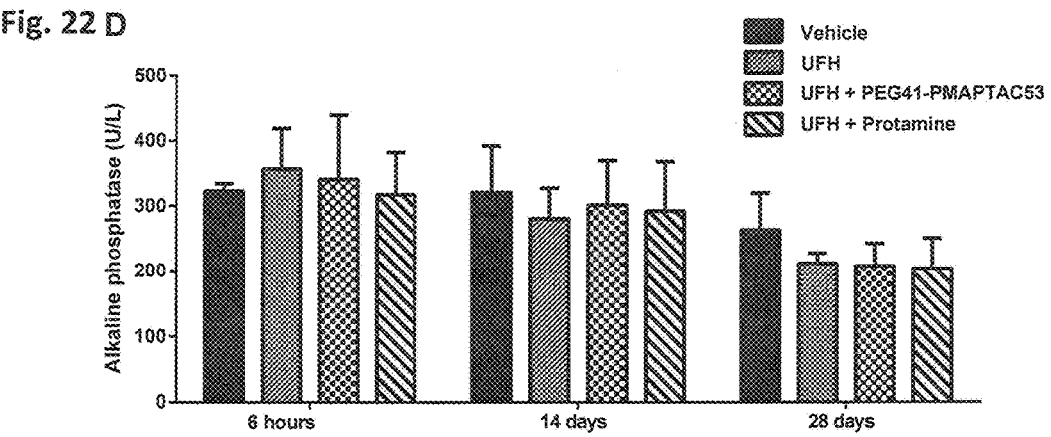
Figure 22:
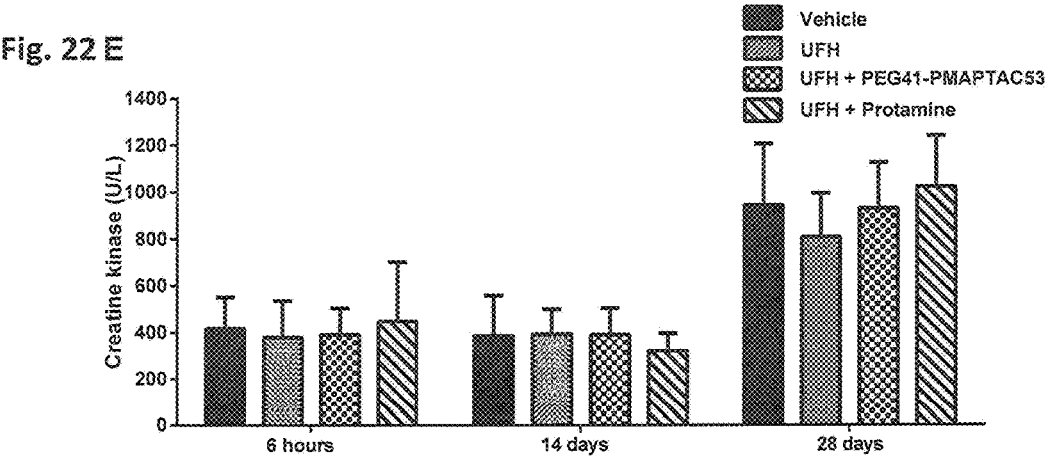

FIG. 22 show the influence of the polymer on hepatic enzymes: aspartate transaminase (AST) (A), alanine transferase (ALT) (B), amylase (C), alkaline phosphatase (D), creatine kinase (E) 6 hours, 7, 14 and 28 days after administration of 300 U/kg unfractionated heparin (UFH), 300 U/kg UFH+1.95 mg/kg PEG41-PMAPTAC53 and 300 U/kg UFH+3 mg/kg protamine.

FIG. 23 shows the examples of histological specimen of rat lungs and liver 1 hour after administration of PBS (A, B), unfractionated heparin (UFH) (C, D) UFH with protamine (E, F) or with PEG41-PMAPTAC53 (G, H) and 28 days after administration of UFH with protamine (I, J) or with PEG41-PMAPTAC53 (K, L).

BEST MODE FOR CARRYING OUT THE INVENTION

The invention is presented in the examples which do not limit its scope.

Example 1. Preparation of Block Copolymers Containing a PMPC Block and a PMAPTAC Block (PMPC-PMAPTAC)

a) Synthesis of PMPC Block (PMPC100-CTA)

15.0 g MPC was dissolved in 45.7 ml of water and then 0,142 g of 4-cyanopentanoic acid dithiobenzoate (CPD) and 71.2 mg of 4,4-azobis(4-cyanopentanoic acid) (V-501). The solution was degassed by bubbling argon for 30 minutes. The polymerization was carried out for 4 hours at 70° C. The obtained mixture was dialyzed against distilled water for five days. The obtained homopolymer (PMPC100-CTA) was isolated using a lyophilizer. The number average molecular weight of the obtained polymer determined with gel chromatography (GPC) was $M_n=1.91\times10^4$ g/mol, while the dispersity of molecular weights ($M_w/M_n$) was 1.05. The polymer was also characterized using $^1$H NMR spectroscopy and it was found that the number average molecular weight, $M_n$, was $2.98\times10^4$, while the degree of polymerization, DP, was 100. The polymer obtained was used to synthesize a diblock copolymer PMPC100-PMAPTAC93.

b) Synthesis of PMPC-PMAPTAC Diblock Copolymers

In 10 ml of water dissolved was 1.09 g 3-methacryloylaminopropylotrimethylammonium chloride (MAPTAC), 7 mg V-501 and 1 g PMPC100-CTA obtained using the procedure described above. The solution was degassed by bubbling argon for 30 minutes. The polymerization was carried out for 6 hours at 70° C. The obtained mixture was dialyzed against distilled water for two days. The obtained block polymer (PMPC100-PMAPTAC93) was isolated using a lyophilizer, The number average molecular weight of the obtained polymer determined using gel chromatography (GPC) was $M_n=9.91\times10^4$ g/mol, while the dispersity of molecular weights ($M_w/M_n$) was 1.11. The polymer was also characterized using $^1$H NMR spectroscopy and it was found that the number average molecular weight, $M_n$, was $4.99 \times 10^4$, while the degree of polymerization, DP, of PMAPTAC block was 93.

Example 2. Synthesis of Block Polymers Containing a PEG Block and a PMAPTAC Block (PEG-PMAPTAC)

a) Synthesis of PEG Homopolymer (PEG41-CTA)

5.66 g N,N'-dicyclohexylcarbodiimide (DCC) in 100 ml dichloromethane was added with a dropper for 30 minutes into the mixture containing 27.4 g methyl ether of polyethylene glycol (MeOPEG) with molecular weight of 2000 g/mol, 4.60 g CPD and traces of 4-dimethylaminopyridine in 100 ml dichloromethane. For next 20 hours the reaction mixture was mixed in 40° C. Then the product was purified from dicyclohexylurea precipitate. The solvent was removed on a rotary evaporator, and the crude product was purified using chromatography on a silicagel and chloroform/methanol eluent (95/5 v/v). $^1$H NMR (CDCl3, δ): 2.17 (s, 3H), 2.40-2.74 (m, 4H), 3.38 (s, 3H), 3.45-4.25 (m, 188H), 4.27 (t, 2H), 7.40 (t, 2H), 7.57 (t, 1H), 7.90 (d, 2H). This polymer was used in the synthesis of diblock polymers PEG41-PMAPTAC53 and PEG41-PMAPTAC21.

b) Synthesis of PEG-PMAPTAC Diblock Polymer

In 30.3 ml dissolved was 5.96 g MAPTAC, 35.0 mg V-501 and 565 mg PEG-CTA obtained according to the procedure described above. The solution was degassed by bubbling argon for 30 minutes. The polymerization was carried out at 70° C. for 5 hours. The reaction mixture was poured into acetone to precipitate the product. The polymer was further purified by dissolving in methanol and precipitation with acetone twice. The purified diblock polymer was dried for 24 hours at 60° C. Based on gel chromatography (GPC) it was found that the number average molecular weight was $M_n = 1.51 \times 10^4$ g/mol, while the dispersity of molecular weight ($M_w/M_n$) was 1.02.

TABLE 1

Characteristics of the polymers obtained from MPC and MAPTAC monomers

| $DP_{PMPC}$ | $DP_{PMAPTAC}$ | $M_n$ (GPC) | $M_n$ (NMR) | $M_w/M_n$ |
|---|---|---|---|---|
| 100 | 93 | 21869 | 50335 | 1.098 |
| 20 | 94 | 20700 | 27000 | 1.03 |
| 20 | 94 | 18300 | 27000 | 1.03 |
| 0 | 198 | 26302 | 43986 | 1.048 |

TABLE 2

Characteristics of PEG-PMAPTAC polymers

| $DP_{PEG}$ | $DP_{PMAPTAC}$ | $M_n$ (GPC) | $M_n$ (NMR) | $M_w/M_n$ |
|---|---|---|---|---|
| 41 | 27 | 8161 | 8321 | 1.028 |
| 41 | 53 | 11130 | 14061 | 1.022 |

Example 3. Synthesis of PMAPTAC Homopolymer

In 30.3 ml of water dissolved was 5.96 g PMAPTAC, 25.0 mg V-501 and 55.1 mg CPD. The solution was degassed by bubbling argon for 30 minutes. The polymerization was carried out for 5 hours at 70° C. The reaction mixture was poured into acetone in order to precipitate the product. The polymer was further purified by dissolving in methanol and precipitation with acetone twice. The purified polymer was dried for 24 hours at 60° C. Based on $^1$H NMR spectra it was found that the number average molecular weight of the polymer was $M_n = 43986$, while the dispersity of the molecular weight (Mw/Mn) was 1.05, and the polymerization degree, DP, was 198.

Example 4. Complexation of Unfractionated Heparin (UFH) by PEG-PMAPTAC and PMPC-PMAPTAC Polymers The dependence of the concentration of free (uncomplexed) unfractionated heparin (UFH) on the concentration of block polymers PEG41-PMAPTAC53, PEG41-PMAPTAC21, PMPC100-PMAPTAC93, and PMPC20-PMAPTAC94 was found using the spectrophotometric method based on the application of Azure A. The plot of the dependence of UFH concentration on the polymer/UFH mass ratio is shown in FIG. 1.

The masses of polymers required to bind 1 mg of heparin calculated using the above plots are collected in the table below.

TABLE 3

Masses of synthesized polymers and protamine required to bind 1 mg of UFH heparin

| Polymer | Mass of polymer required to bind 1 mg of UFH heparin |
|---|---|
| PEG41-PMAPTAC53 | 0.65 mg |
| PEG41-PMAPTAC21 | 3.12 mg |
| PMPC20-PMAPTAC94 | 0.75 mg |
| PMPC100-PMAPTAC93 | 2.58 mg |
| protamine | 1.26 mg |

Example 5. The DLS Measurements of the Size of the Complexes of Synthesized Polymers with UFH Using dynamic light scattering technique (DLS) the size of the complexes of the polymers with UFH heparin in PBS was measured. The proportion of the volumes and concentrations used corresponds to the spectrophotometrically calculated amount of the polymer necessary to completely bind heparin. The results of the DLS measurements of the size of the complexes formed by the polymers and UFH are shown in FIG. 2.

It was confirmed, that complexes of all polymers with UFH (excluding PEG41-PMAPTAC21) are smaller than complexes of protamine with UFH (1300 nm), with rather slight dispersity.

Example 6. Zeta Potential of Examined Polymers and their Complexes with Heparin Table 4 shows measurement of the zeta potential of tested polymers and their complexes with heparin.

TABLE 4

Zeta potential of polymers and their complexes with heparin in PBS solutions.

| Polymer | Zeta potential [mV] | Zeta potential of polymer complexes with UFH [mV] |
|---|---|---|
| PEG41-PMAPTAC53 | +7.27 | −7.94 |
| PEG41-PMAPTAC21 | +9.82 | +1.28 |
| PMPC20-PMAPTAC94 | +9.11 | −13.13 |
| PMPC100-PMAPTAC93 | +10.95 | −2.08 |

Example 7. Binding of Polymers with Bovine Serum Albumin

The size of protamine and examined polymer's complexes with bovine serum albumin was measured using dynamic light scattering (DLS) technique. The measurement showed that the maximal size of polymers complexes is significantly smaller than the size of protamine's complexes.

Because small complexes will not clot the blood vessels, especially capillaries, and will be easier eliminated, the use of polymers according to discovery seems to be significantly safer than the use of protamine. FIG. 3 shows the results of DLS measurements of protamine and examined polymer's complexes with bovine serum albumin.

Example 8. Neutralization of Unfractionated Heparin by Polymers In Vivo

The study was performed on Wistar rats, in which the arterial thrombosis was induced. Examined compounds were administered 3 minutes after administration of heparin. Ten minutes after administration of heparin the electrical stimulation of prepared common carotid artery of rat started (1 mA), and was continued for next 10 minutes. 45 min after electrical stimulation the blood and 1 cm of the damaged carotid artery was collected, the formed thrombus removed, dried at room temperature and weighed 24 h after the end of the experiment. The thrombus weight in the control group (animals receiving PBS) was around 0.9 mg. Unfractionated heparin administered at a dose of 300 IU/kg decreased thrombus weight by 41%. All studied polymers similarly to protamine diminished the antithrombotic effect of heparin. The neutralization of thrombus weight and bleeding time to control values presents FIG. 4 and FIG. 5. The collected blood was centrifuged, and platelet poor plasma was further used to measure the effect of heparin and examined polymers on coagulation parameters.

UFH prolonged activated partial thromboplastin time (aPTT) to 300 seconds, and anti-factor Xa activity increased seven times. These both parameters were restored to control values after injection of polymers (FIG. 6 and FIG. 7, respectively), and the activity of most polymers neutralizing effect of heparin on anti-factor Xa activity was stronger in comparison to protamine and DEX40-GTMAC3.

Example 9. The Effect of Polymers on Hematologic Parameters in Rats with Induced Arterial Thrombosis We evaluated the effect of polymers on hematologic parameters 1 hour after their administration together with unfractionated heparin to Wistar rats with induced arterial thrombosis. In blood collected from the heart of rats in the experiment of example 8 hematologic parameters were measured (FIG. 8). The most similar activity to protamine exerted PEG41-PMAPTAC53 (no significant changes of studied parameters, with simultaneous reversing of the increase in WBC as an effect of unfractionated heparin administration).

Example 10. The Effect of Studied Polymers on Arterial Blood Pressure

The most frequent adverse effect of protamine use is hypotension with bradycardia. It is particularly dangerous during all surgeries under general anesthesia when the blood pressure drops in response to inhaled anesthetic, and the maintaining of all vital functions on the steady level is the main issue.

The experiment evaluating the effect of polymers according to discovery and protamine on the arterial blood pressure was performed. The study was carried in Wistar rats under general anesthesia (pentobarbital, 50 mg/kg i.p.), in which the blood pressure was measured directly in the carotid artery with Hugo Sachs (Plugsys, Transonics System, USA) equipment. Examined compounds were administered into rats 3 minutes after heparin and the blood pressure was monitored for 60 minutes (FIG. 9).

The results of the experiment showed that the PEG41-PMAPTAC53 and PMPC100-PMAPTAC93 have no effect on blood pressure. Thus, the risk of hypotension after administration of these polymers to patients according to discovery will be minimized or eliminated. Above examples indicate that all examined polymers efficiently neutralize the effect of unfractionated heparin.

Because of the similar effects of all polymers and the fact, that PEG41-PMAPTAC53 has the most favorable ratio of efficacy to toxicity, this polymer was chosen as a representative of all polymer groups according to discovery. Additionally, this allowed reducing the number of animals in the experiments.

Next examples show that these polymers may replace the use of protamine in patients requiring neutralization of heparin, especially unfractionated and low-molecular-weight heparin (LMWH).

Example 11. Complexing of Enoxaparin (Clexane) a Low-Molecular-Weight Heparin (LMWH) by PEG41-PMAPTAC53

We measured binding of free (uncomplexed) enoxaparin by PEG41-PMAPTAC53 using colorimetric method of Azure A. The concentration-dependent changes of PEG41-PMAPTAC53/enoxaparin are presented in FIG. 10. Based on the binding curve we estimated that 0.85 mg of PEG41-PMAPTAC53 binds 1 mg of enoxaparin.

Example 12. Neutralization of Enoxaparin (Clexane) a Low-Molecular-Weight Heparin (LMWH) by PEG41-PMAPTAC53 In Vitro This example shows neutralization of the effect of enoxaparin on anti-fXa activity by PEG41-PMAPTAC53 at in vitro conditions. The results of the activity of anti-fXa increased by enoxaparin incubated with different concentrations of PEG41-PMAPTAC53 in 96-wells polystyrene plate are presented in FIG. 11.

The experiment showed that PEG41-PMAPTAC53 diminished the effect of enoxaparin (the enhancement of anti-fXa activity). Additionally, the ratio of polymer to enoxaparin was estimated, which enabled to choose appropriate dose for in vivo study. The example also shows the advantage of discovery over the protamine, which in patients (http://www.biomed.com.pl/plik/4bac945be0f1b-ulotka_Siarczanprotaminy.pdf) or similar study in the rat (Shenoi at al. Sci Transl Med., 2014) only partially neutralizes the action of enoxaparin.

Example 13. Neutralization of Enoxaparin (Clexane) a Low-Molecular-Weight Heparin (LMWH) by PEG41-PMAPTAC53 In Vivo The studies were performed on Wistar rats. Five minutes after heparin examined polymers were infused for 5 minutes.

In time points: 0, 5, 10, 15, 30 and 60 minutes activation clotting time (ACT) was measured with Hemochron Junior in 2 blood drops from rat tail. Intravenously administered enoxaparin in a dose of 3 mg/kg almost twice time prolonged ACT. Five minutes after administration PEG41-PMAPTAC53 restored ACT to starting value, and the effect lasted to the end of observation (FIG. 12).

The examples 12 and 13 show that PEG41-PMAPTAC53 can neutralize low-molecular-weight heparin in 100%. Thus, it may be a safe and efficient antidote for anticoagulant effect of LMWH. In that way, the indications for the use of LMWH may expand to the procedures in which the unfractionated heparin is used. During experiments, authors observed that polymers according to discovery exert high efficacy of heparin neutralization with full biocompatibility and may become an excellent alternative to other methods of heparin neutralization, especially currently used protamine. Next examples confirm author's observations.

Example 14. Evaluation of Tissue Distribution of PEG41-PMAPTAC53 in Mice

The perfect antidote should exert its effect rapidly (enabling fast help), it should distribute only in the blood compartment, where it should bind heparin (no organ accumulation limits the risk of damage), and next, the complexes of polymer with heparin or free polymer should be rapidly eliminated with urine (in contrast to long action, which makes impossible to react in case of potential adverse effects, fast and short action enables controlled use of antidote with repeated administration of lower doses if needed). Based on the chemical structure, we assumed that ionic and high molecular weight compound would distribute mainly in the blood. The important issue is also the size of formed complex of heparin with the antidote. The measurements showed that complexes of heparin with PEG41-PMAPTAC53 are smaller than complexes of heparin with protamine. It also suggests that in comparison to protamine, the elimination of heparin/PEG41-PMAPTAC53 complexes should be faster with a small degree of organ accumulation, such as liver, kidneys or lungs. Thus, the safety profile of PEG41-PMAPTAC53 should be better than protamine.

To confirm this hypothesis, we performed tissue distribution studies of PEG41-PMAPTAC53, as a representative of polymer's group in mice. The polymer was conjugated with Alexa Fluor® 750, and next intravenously administered to 30 NMRI-Foxnlnu/Foxnlnu mice. The signal of labeled polymer was measured after 0, 5, 30, 60 and 120 minutes (5 animals for every time point) by In-vivo MS FX PRO (Carestream Health INC., USA). The fluorescence intensity was compared to the control groups, which was treated only with vehicle. The highest signal in the area of the bladder on the beginning and decrease of fluorescence over time of observation indicates that the examined polymer was rapidly excreted in urine (FIG. 13 and FIG. 14). In contrast to the polymer, the fluorescence of protamine in the area of the bladder was weak. Small amounts of labeled PEG41-PMAPTAC53 was found in the highly blood perfused organs (liver and kidneys), although the fluorescence was much weaker in comparison to protamine (FIG. 15).

This example shows, that polymers according to discovery exert fast and short action, and do not accumulate in the organs after intravenous administration. In contrast, protamine seems to accumulate in the liver. Thus, the negative effect on this tissue cannot be excluded. The permanent changes could occur in the highly blood perfused organs especially after repeated administration. Better bioavailability of polymers in comparison to protamine according to discovery will improve the safety of heparin neutralization and will limit the risk of eventual complications.

The results of fluorescence imaging of liver and kidney collected from mice receiving labeled PEG41-PMAPTAC53 at various time points are presented in FIG. 16 (the organ from animals treated with the vehicle is located in the lower left corner of the image).

The results of fluorescence imaging of liver and kidney collected from mice receiving labeled protamine at various time points are presented in FIG. 17 (the organ from animals treated with the vehicle is located in the lower left corner of the image).

The results of fluorescence imaging of rhodamine-labeled protamine in mice presented in FIG. 17 and FIG. 18 indicate clear accumulation of protamine in most organs. The accumulation may result in tissue damage, which was found in histopathological examination. The intensity of fluorescence signal from rhodamine-labeled protamine in collected organs is presented in FIG. 18.

Example 15. The Evaluation of Acute Cardio-Respiratory Toxicity of PEG41-PMAPTAC53 in Rats The effect of PEG41-PMAPTAC53 on main vital parameters was measured 1 hour after concomitant intravenous administration with UFH. Arterial blood pressure, heart rate, tissue perfusion of rat's paw, respiratory rate, blood oxygen saturation, peak exhaled $CO_2$, and body temperature were monitored for 1 hour. PEG41-PMAPTAC53 administered in 3 times higher than therapeutic dose (5.85 mg/kg) decreased blood pressure by 20% and simultaneously increased tissue perfusion (the increase lasted 15 minutes, and then returned to the starting point (FIG. 19). The similar effect was observed after administration of protamine in 3 times higher than the therapeutic dose. Other parameters did not change during the experiment. None of the measured parameters changed when the injection of PEG41-PMAPTAC53 was replaced by 5-minute infusion. Both, blood pressure and tissue perfusion returned to normal level.

According to Summary of Product Characteristics, the adverse effects of protamine primarily include cardiovascular complications (http://www.biomed.com.pl/plik./4bac945be0f1b-ulotka_Siarczanprotaminy.pdf). The most frequent are hypotension and bradycardia. The mechanism of these reactions may depend on the L-arginine released from the molecule of protamine, which is endogenous precursor and substrate of NO synthesis, one of the strongest vasodilators. Additionally, respiratory dysfunction, bronchospasm, and difficulties with breathing may occur after protamine administration. Thus, we evaluated the effect of PEG41-PMAPTAC53 as a representative of polymer's group without L-arginine in its structure on main vital cardio-respiratory parameters. PEG41-PMAPTAC53 infused in 3 times higher than effective dose (5.85 mg/kg) did not change any of cardio-respiratory parameters. Thus, according to discovery, the risk of cardiovascular and respiratory adverse effects typical for protamine was eliminated or at least significantly reduced.

Example 16. The Evaluation of PEG41-PMAPTAC53 Effects on Blood at In Vitro Conditions The effect of PEG41-PMAPTAC53 on blood parameters (WBC, RBC, HGB, HCT, MCV, MCH, MCHC, PLT) at in vitro conditions 30 minutes after incubation of blood with the polymer in concentrations of 1, 10 and 100 μg/ml was studied. No clinically significant changes were observed (FIG. 20).

Example 17. The Evaluation of PEG41-PMAPTAC53 Effect on Hematologic Parameters at In Vivo Conditions Charged macromolecules may cause hemolysis. To estimate polymer safety according to discovery hematologic parameters were measured at in vivo conditions after administration of PEG41-PMAPTAC53 as a representative of polymer's group with unfractionated heparin (FIG. 21). Blood count was performed in rat blood collected after 7, 14 and 28 days from polymer injection.

No statistically significant changes were found. Thus, polymers do not exert blood toxicity.

Example 18. The Evaluation of Acute and Chronic Organ Toxicity of PEG41-PMAPTAC53 in Rats: Serum Concentration of Biochemical Parameters The effects of PEG41-PMAPTAC53 as a representative of polymer's group and protamine on main organ function of rats up to 28 days from single injection were studied to estimate the safety of polymer use according to discovery. The evaluation of toxicity included once a week measurement of rat's serum concentration of classical markers confirming organ dysfunction. The concentration of examined biochemical parameters in rat's serum, such as AST, ALT, creatinine, amylase, alkaline phosphatase, and creatine phosphokinase did not change for one month from a single injection of polymer and protamine (FIG. 22).

The results indicate the neutral effect of polymers according to discovery on functions of internal organs, such as liver, kidneys, pancreas, bones and muscles.

Example 19. The Evaluation of Acute and Chronic Organ Toxicity of PEG41-PMAPTAC53 in Rats: Histopathological Analysis Besides tissue distribution, the histopathological evaluation of acute and chronic organ toxicity should be performed before entering into clinical trials. Because of the route of administration of antidote (single intravenous administration), is seems that evaluation of animals from 1 hour to 28 days after single intravenous injection resembles the most clinical scenario. According to guidelines of drug agencies, the toxicity should be estimated by measuring of blood hematology and markers of organ dysfunction. The macro- and microscopic organ evaluation are also essential. These experiments are performed to predict potential toxicity in clinical studies. Protamine and heparin complexes together with platelets may clot pulmonary arteries, activate the complement system and bronchospasm. It was shown that protamine may induce severe asthma attack due to the release bronchoactive substances, e.g. histamine. Pulmonary hypertension induced by protamine/heparin complexes may be caused by edema and hemorrhage, and resulting disorders, such as hypoxemia, blood platelets accumulation, leukocyte and complement activation.

According to discovery, the effect of polymers on the main internal organs of the rat was studied using PEG41-PMAPTAC53 as a representative of polymer's group.

Lungs and liver were collected from Wistar rats 1 hour or 28 days after unfractionated heparin followed by PEG41-PMAPTAC53 or protamine administration. In animals treated with protamine and heparin strong pulmonary hemorrhage and necrotic changes in the liver were observed 1 hour after administration (FIG. 23). The pulmonary hemorrhage was less pronounced, but liver necrosis was still present after 28 days. In rats injected with unfractionated heparin and PEG41-PMAPTAC53 slight lung congestion, an increase of eosinophilic cytoplasm, slight vacuolization, and multinuclear cells were present. These changes disappeared after 28 days.

Histopathological examination did not reveal higher organ toxicity of PEG41-PMAPTAC53 in comparison to protamine. Fast elimination in urine and transient changes of hepatocytes point on lower nephro- and hepatotoxicity of the polymer according to discovery. Pulmonary vascular changes are probably caused by complexes of polymer/heparin. However, these changes are less pronounced, possibly because the complexes of protamine/heparin are larger than complexes of PEG41-PMAPTAC53 according to discovery.

The invention claimed is:

1. A method for the direct neutralization of heparins in blood and body fluids comprising
applying a block copolymer containing poly(3-(methacryloylamino)propyltrimethylammonium chloride) (PMAPTAC), as one block of the block copolymer to the blood and body fluids containing heparins.

2. The method according to claim 1, wherein the block copolymer is poly(ethylene glycol)-block-poly(3-(methacryloylamino)propyltrimethylammonium chloride) (PEG-PMAPTAC).

3. The method according to claim 1, wherein the block copolymer is poly(2-(methacryloyloxy)ethyl phosphorylcholine-block-poly(3-(methacryloylamino)propyltrimethylammonium chloride) (PMPC-PMAPTAC).

4. The method according to claim 1, wherein the block polymers comprising PMAPTAC are prepared by a method of controlled radical polymerization (CRP).

5. The method according to claim 2, wherein the copolymer PEG-PMAPTAC is selected from the group consisting of PEG41-PMAPTAC53 and PEG41-PMAPTAC21.

6. The method according to claim 3, wherein the copolymer PMPC-PMAPTAC is selected from the group consisting of PMPC20-PMAPTAC94 and PMPC100-PMAPTAC93.

7. The method according to claim 1, wherein the heparins are selected from the group consisting of unfractionated heparin, and low-molecular-weight heparin.

8. The method according to claim 7, wherein the block copolymer is PEG-PMAPTAC.

9. The method according to claim 8, wherein the copolymer PEG-PMAPTAC is selected from the group consisting of PEG41-PMAPTAC53 and PEG41-PMAPTAC21.

10. The method according to claim 7, wherein the block copolymer is PMPC-PMAPTAC.

11. The method according to claim 10, wherein the copolymer PMPC-PMAPTAC is selected from the group consisting of PMPC20-PMAPTAC94 and PMPC100-PMAPTAC93.

12. The method according to claim 7, wherein the block polymers comprising PMAPTAC are prepared by a method of controlled radical polymerization (CRP).

\* \* \* \* \*